(12) United States Patent
Ito

(10) Patent No.: US 10,653,377 B2
(45) Date of Patent: May 19, 2020

(54) BREAST COMPUTED TOMOGRAPHY SYSTEM COMPRISING A GRIPPER

(71) Applicant: CANON KABUSHIKI KAISHA, Tokyo (JP)

(72) Inventor: Nobuhiro Ito, Yamato (JP)

(73) Assignee: Canon Kabushiki Kaisha, Tokyo (JP)

( * ) Notice: Subject to any disclaimer, the term of this patent is extended or adjusted under 35 U.S.C. 154(b) by 270 days.

(21) Appl. No.: 15/533,331

(22) PCT Filed: Dec. 4, 2015

(86) PCT No.: PCT/JP2015/006043
§ 371 (c)(1),
(2) Date: Jun. 5, 2017

(87) PCT Pub. No.: WO2016/092797
PCT Pub. Date: Jun. 16, 2016

(65) Prior Publication Data
US 2018/0008221 A1    Jan. 11, 2018

(30) Foreign Application Priority Data
Dec. 9, 2014    (JP) .................... 2014-249443

(51) Int. Cl.
*A61B 6/00* (2006.01)
*A61B 6/03* (2006.01)
(Continued)

(52) U.S. Cl.
CPC ............ *A61B 6/502* (2013.01); *A61B 5/0073* (2013.01); *A61B 5/0091* (2013.01); *A61B 5/0095* (2013.01); *A61B 5/708* (2013.01); *A61B 6/032* (2013.01); *A61B 6/035* (2013.01); *A61B 6/04* (2013.01); *A61B 6/0414* (2013.01); *A61B 6/0421* (2013.01); *A61B 6/0428* (2013.01);
(Continued)

(58) Field of Classification Search
CPC ........ A61B 6/032; A61B 6/035; A61B 6/0414; A61B 6/0421; A61B 6/0435; A61B 6/502; A61B 6/04; A61B 6/44; A61B 6/4429; A61B 6/4435; A61B 6/4441; A61B 6/4447
USPC .............................. 378/20, 37, 62, 196, 197
See application file for complete search history.

(56) References Cited

U.S. PATENT DOCUMENTS

| 4,979,196 A | 12/1990 | Lieutaud |
| 5,289,520 A * | 2/1994 | Pellegrino ............ A61B 6/0435 378/208 |

(Continued)

FOREIGN PATENT DOCUMENTS

| CN | 101147685 A | 3/2008 |
| CN | 102215752 A | 10/2011 |

(Continued)

*Primary Examiner* — Allen C. Ho
(74) *Attorney, Agent, or Firm* — Canon U.S.A., Inc. IP Division

(57) ABSTRACT

The present invention provides a breast computed tomography system in which the body motion and the pain of an examinee during capturing of images of the breast are reduced. The breast computed tomography system includes a gantry accommodating a light emitting unit that radiates light onto the breast. The gantry includes a gripper having a right gripping portion and a left gripping portion.

30 Claims, 20 Drawing Sheets

(51) Int. Cl.
*A61B 6/04* (2006.01)
*A61B 5/00* (2006.01)
(52) U.S. Cl.
CPC .............. *A61B 6/0435* (2013.01); *A61B 6/44*
(2013.01); *A61B 6/4429* (2013.01); *A61B 6/4435* (2013.01); *A61B 6/4441* (2013.01);
*A61B 6/4447* (2013.01)

(56) References Cited

U.S. PATENT DOCUMENTS

| | | | | |
|---|---|---|---|---|
| 5,386,447 | A * | 1/1995 | Siczek | A61B 6/0414 378/196 |
| 6,298,114 | B1 * | 10/2001 | Yoda | A61B 6/0414 378/37 |
| 6,463,122 | B1 * | 10/2002 | Moore | A61B 6/0435 378/17 |
| 6,480,565 | B1 * | 11/2002 | Ning | A61B 6/032 378/20 |
| 6,748,044 | B2 * | 6/2004 | Sabol | G06T 7/0012 250/363.04 |
| 6,987,831 | B2 * | 1/2006 | Ning | A61B 6/032 378/20 |
| 6,999,554 | B2 * | 2/2006 | Mertelmeier | A61B 6/502 378/196 |
| 7,017,209 | B1 | 3/2006 | De Jong | |
| 7,298,816 | B2 * | 11/2007 | Moore | A61B 6/4441 378/197 |
| 7,302,031 | B2 * | 11/2007 | Hjärn | A61B 6/02 378/23 |
| 7,317,822 | B2 * | 1/2008 | Kurahashi | A61B 6/484 378/37 |
| 7,492,858 | B2 * | 2/2009 | Partain | A61B 6/032 378/196 |
| 7,519,149 | B2 * | 4/2009 | Mackie | A61N 5/1042 378/37 |
| 7,545,907 | B2 * | 6/2009 | Stewart | A61B 6/02 378/108 |
| 7,561,661 | B2 * | 7/2009 | Ullberg | A61B 6/032 378/19 |
| 7,597,477 | B1 | 10/2009 | Hosseinian | |
| 7,649,981 | B2 * | 1/2010 | Seppi | A61B 6/032 378/124 |
| 7,668,287 | B2 * | 2/2010 | Sendai | A61B 5/0091 378/15 |
| 7,676,021 | B2 * | 3/2010 | Tsujii | A61B 6/032 378/17 |
| 7,742,796 | B2 * | 6/2010 | Eberhard | A61B 6/502 378/37 |
| 7,764,762 | B2 * | 7/2010 | Sendai | A61B 5/0091 378/19 |
| 7,769,130 | B2 * | 8/2010 | Nakata | A61B 6/502 378/195 |
| 7,817,773 | B2 * | 10/2010 | Stanton | A61B 6/466 378/15 |
| 7,831,015 | B2 * | 11/2010 | Li | A61B 6/032 378/37 |
| 7,864,918 | B2 * | 1/2011 | Schilling | G06T 7/12 378/196 |
| 7,869,563 | B2 * | 1/2011 | Defreitas | A61B 6/107 378/37 |
| 7,869,862 | B2 * | 1/2011 | Seppi | A61B 6/032 600/420 |
| 7,885,379 | B2 * | 2/2011 | Meer | A61B 6/502 378/37 |
| 7,957,503 | B2 * | 6/2011 | Kobayashi | A61B 6/0414 378/209 |
| 7,957,508 | B2 * | 6/2011 | Brooks | A61B 6/502 378/37 |
| 8,014,490 | B2 * | 9/2011 | Mitchell | A61B 6/502 378/196 |
| 8,130,906 | B2 * | 3/2012 | Sendai | A61B 6/0435 378/37 |
| 8,139,712 | B2 * | 3/2012 | Kojima | A61B 6/0414 378/116 |
| 8,374,312 | B2 * | 2/2013 | Mansfield | A61B 6/0414 378/20 |
| 8,391,572 | B2 * | 3/2013 | Morita | A61B 6/502 382/128 |
| 8,465,204 | B2 * | 6/2013 | Kamiya | A61B 10/0275 378/204 |
| 8,467,495 | B2 * | 6/2013 | Okada | A61B 6/022 378/151 |
| 8,553,833 | B2 * | 10/2013 | Flohr | A61B 6/032 378/15 |
| 8,559,590 | B2 * | 10/2013 | Partain | A61B 6/032 378/21 |
| 8,594,275 | B2 * | 11/2013 | Matsuura | A61B 6/0414 378/208 |
| 8,649,479 | B2 * | 2/2014 | De Man | A61B 6/032 378/16 |
| 8,712,012 | B2 * | 4/2014 | O'Connor | A61B 6/03 378/208 |
| 8,774,354 | B2 * | 7/2014 | Ullberg | A61B 6/032 250/491.1 |
| 8,787,522 | B2 * | 7/2014 | Smith | A61B 6/025 378/37 |
| 8,792,965 | B2 * | 7/2014 | Ning | A61B 6/032 600/427 |
| 8,804,903 | B2 * | 8/2014 | Hoernig | A61B 6/502 378/208 |
| 8,824,625 | B2 * | 9/2014 | Ullberg | A61B 6/0435 378/19 |
| 8,825,135 | B2 * | 9/2014 | Okada | A61B 6/00 600/407 |
| 8,838,207 | B2 * | 9/2014 | Nakayama | A61B 6/0414 378/147 |
| 8,842,806 | B2 * | 9/2014 | Packard | A61B 6/025 378/195 |
| 8,848,865 | B2 * | 9/2014 | Nakayama | A61B 6/0414 378/37 |
| 8,855,745 | B2 * | 10/2014 | Hoernig | A61B 6/032 600/431 |
| 8,918,932 | B2 * | 12/2014 | Taku | A61B 5/0091 378/209 |
| 8,942,782 | B2 * | 1/2015 | Sakaguchi | A61B 6/022 378/6 |
| 9,113,792 | B2 * | 8/2015 | Jang | A61B 6/5252 |
| 9,161,725 | B1 * | 10/2015 | Millien-White | A61B 6/0407 |
| 9,364,191 | B2 * | 6/2016 | Ning | A61B 6/032 |
| 9,380,990 | B2 * | 7/2016 | Kim | A61B 6/502 |
| 9,392,986 | B2 * | 7/2016 | Ning | A61B 6/032 |
| 9,439,614 | B2 * | 9/2016 | Jang | A61B 6/03 |
| 9,456,795 | B2 * | 10/2016 | Lee | A61B 6/467 |
| 9,460,823 | B2 * | 10/2016 | Song | H05K 7/2039 |
| 9,510,794 | B2 * | 12/2016 | Kuwabara | G01T 1/24 |
| 9,615,796 | B2 * | 4/2017 | Coucke | A61N 5/10 |
| 9,636,072 | B2 * | 5/2017 | Shores | A61B 6/032 |
| 9,649,068 | B2 * | 5/2017 | DeFreitas | A61B 6/0435 |
| 9,687,151 | B2 * | 6/2017 | Neelakanta | A61B 5/708 |
| 9,724,065 | B2 * | 8/2017 | So | A61B 6/502 |
| 9,820,711 | B2 * | 11/2017 | Tsukuda | A61B 6/547 |
| 9,867,582 | B2 * | 1/2018 | Kim | A61B 6/08 |
| 9,883,839 | B2 * | 2/2018 | Nariyuki | A61B 6/0414 |
| 9,883,845 | B2 * | 2/2018 | Tsujii | A61B 6/502 |
| 9,898,840 | B2 * | 2/2018 | Klausz | G06T 11/006 |
| 9,968,308 | B2 * | 5/2018 | Kawase | A61B 6/032 |
| 10,039,511 | B2 * | 8/2018 | Ito | A61B 6/502 |
| 10,064,592 | B2 * | 9/2018 | Kawase | A61B 6/032 |
| 10,092,358 | B2 * | 10/2018 | Defreitas | A61B 6/025 |
| 10,105,112 | B2 * | 10/2018 | Utsumi | A61B 6/02 |
| 10,299,749 | B2 * | 5/2019 | Fukuda | A61B 6/025 |
| 10,376,229 | B2 * | 8/2019 | Tamura | H05G 1/02 |
| 10,531,846 | B2 * | 1/2020 | MacDonald | A61B 6/502 |
| 2009/0086928 | A1 | 4/2009 | Nakata | |

(56) References Cited

U.S. PATENT DOCUMENTS

| | | |
|---|---|---|
| 2010/0080344 A1 | 4/2010 | Schilling et al. |
| 2011/0200178 A1 | 8/2011 | Mansfield |

FOREIGN PATENT DOCUMENTS

| | | |
|---|---|---|
| CN | 102429678 A | 5/2012 |
| CN | 103179906 A | 6/2013 |
| CN | 203634194 U | 6/2014 |
| CN | 103908295 A | 7/2014 |
| JP | 2000116635 A | 4/2000 |
| JP | 2008-229158 A | 10/2008 |
| JP | 2008307236 A | 12/2008 |
| JP | 2009525093 A | 7/2009 |
| JP | 2010069241 A | 4/2010 |
| JP | 2011206438 A | 10/2011 |
| JP | 2013538668 A | 10/2013 |
| JP | 2014-023681 A | 2/2014 |
| JP | 2014083196 A | 5/2014 |
| WO | 2012008492 A1 | 1/2012 |

\* cited by examiner

[Fig. 1A]
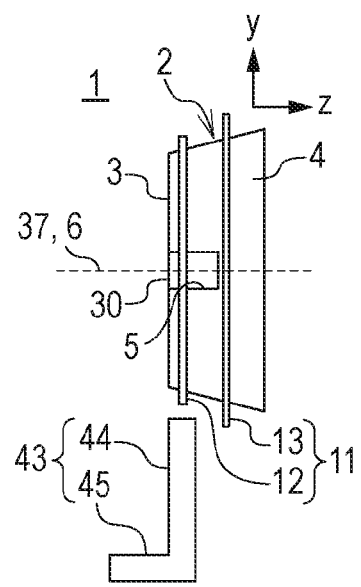
[Fig. 1B]
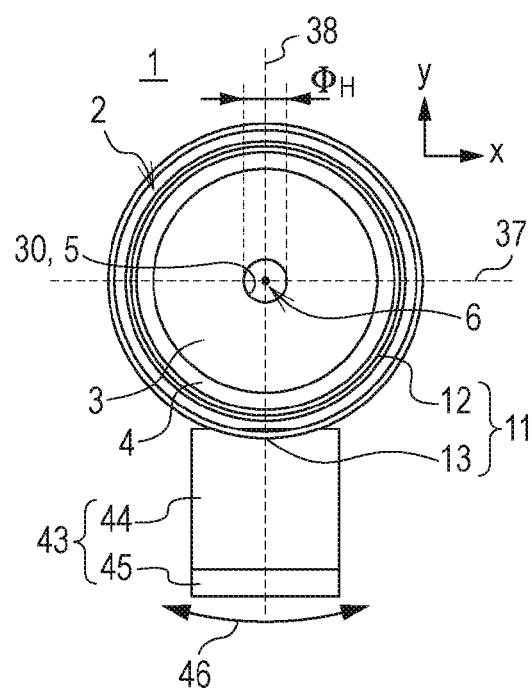

[Fig. 1C]
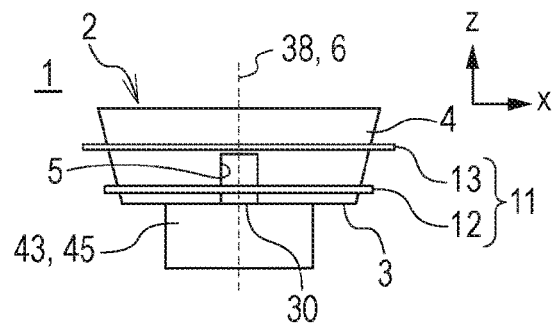
[Fig. 1D]
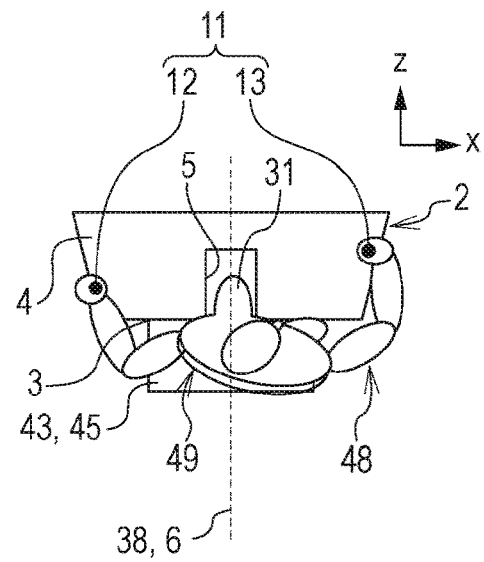
[Fig. 1E]
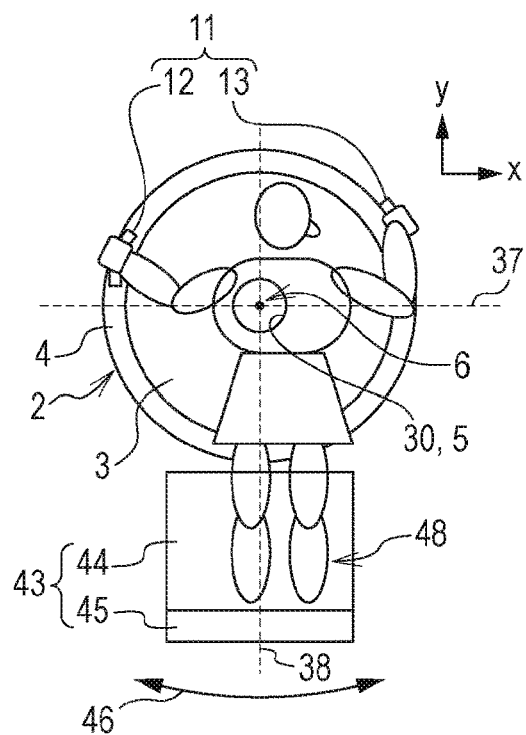

[Fig. 2B]
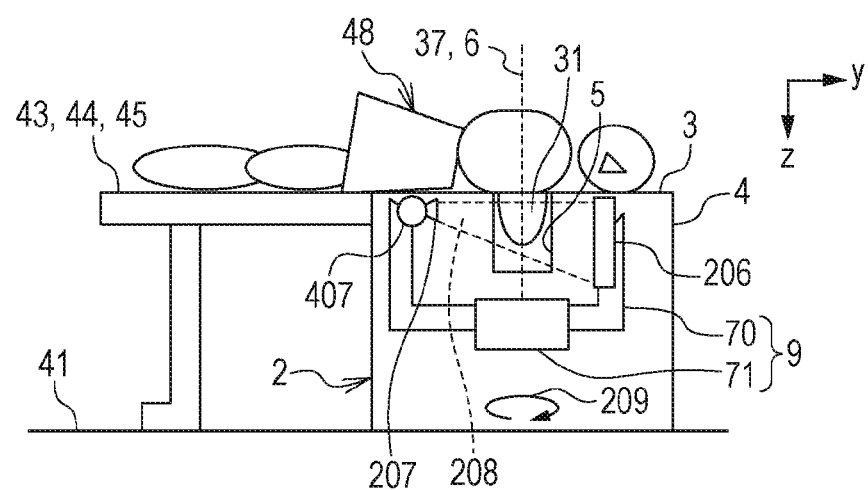
[Fig. 2C]
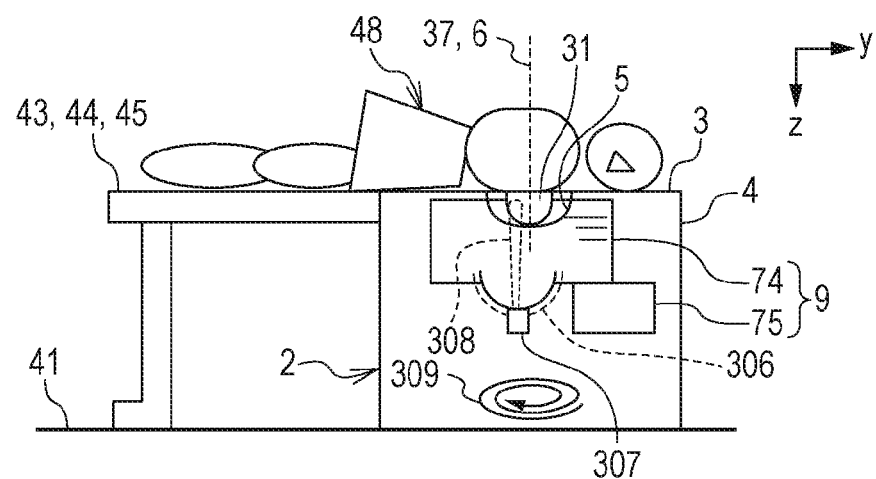

[Fig. 3]
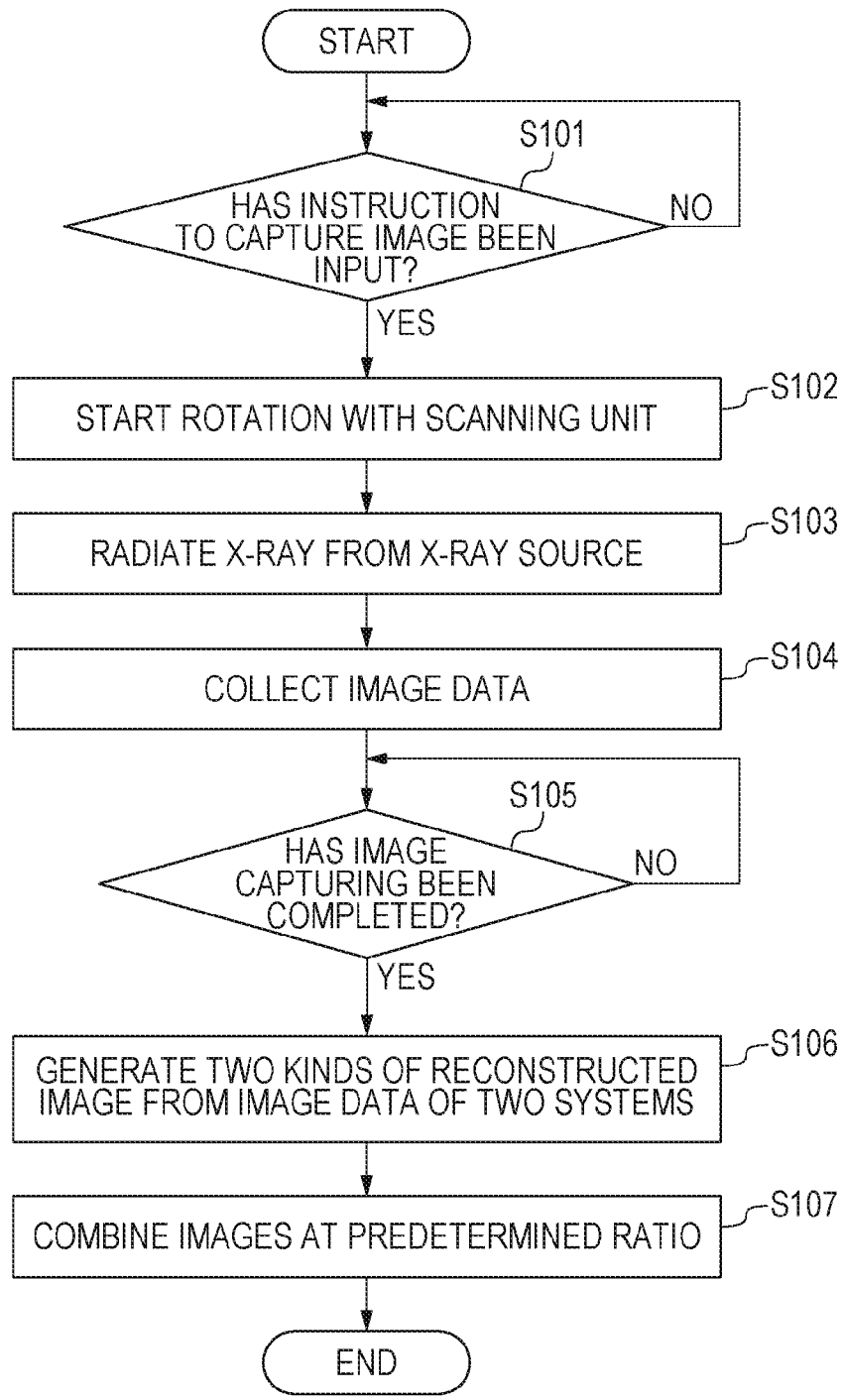

[Fig. 4A]
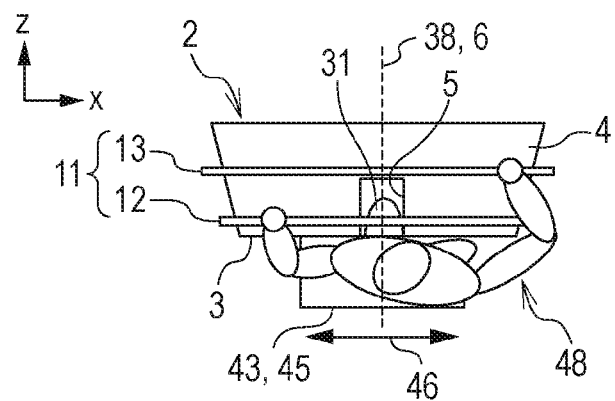
[Fig. 4B]
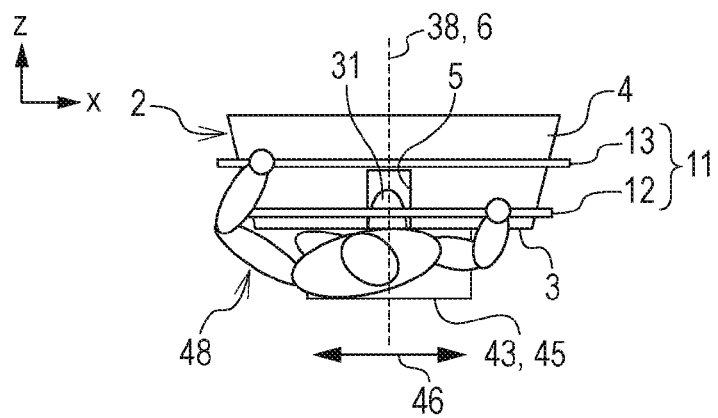

[Fig. 4C]
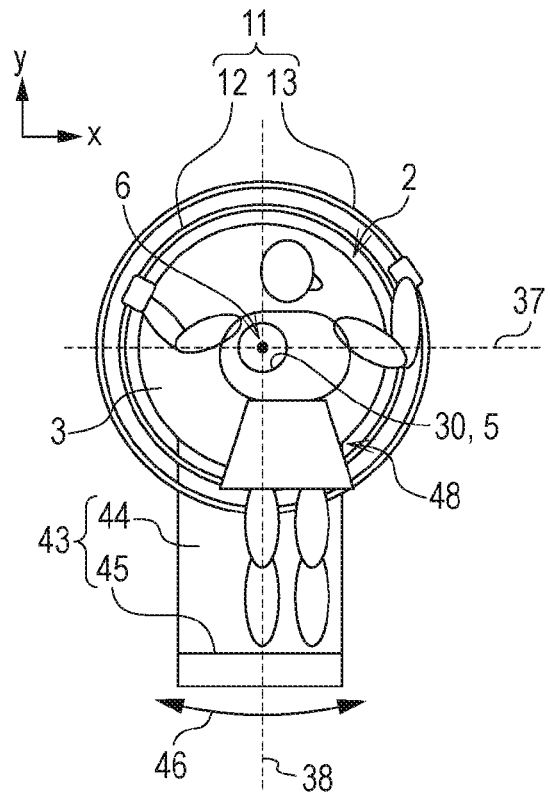
[Fig. 4D]
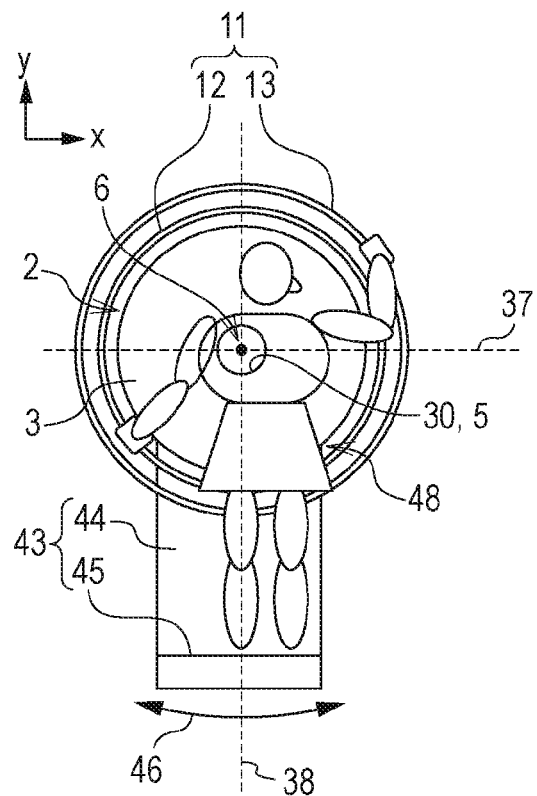

[Fig. 5A]
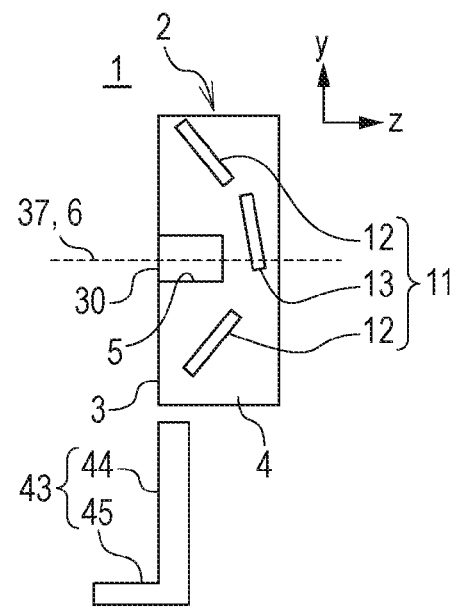
[Fig. 5B]
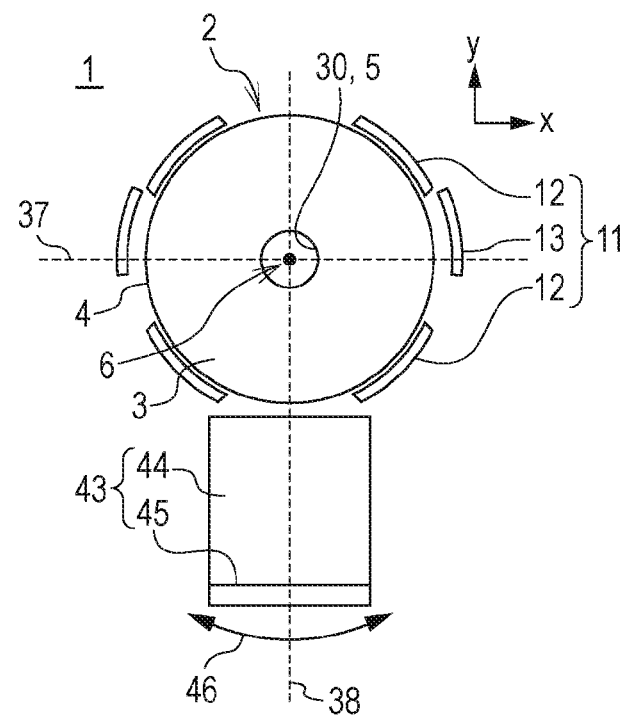

[Fig. 5C]
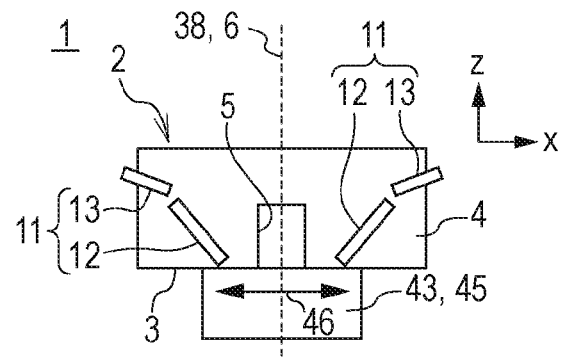
[Fig. 5D]
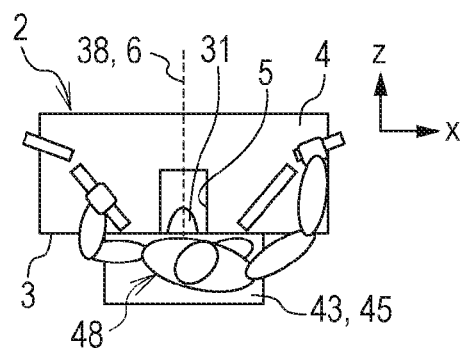
[Fig. 5E]
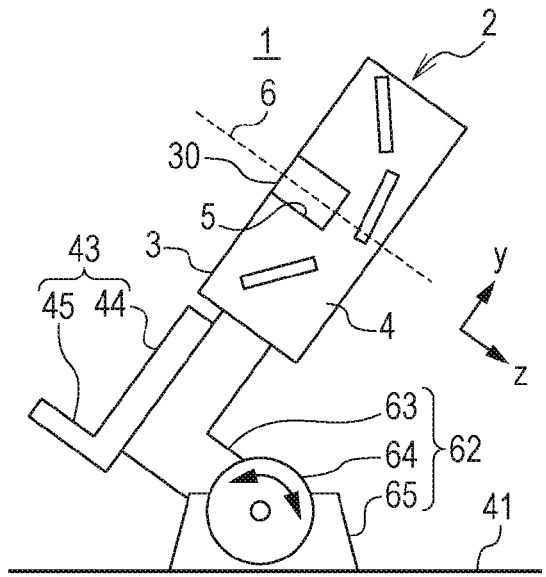

[Fig. 6A]
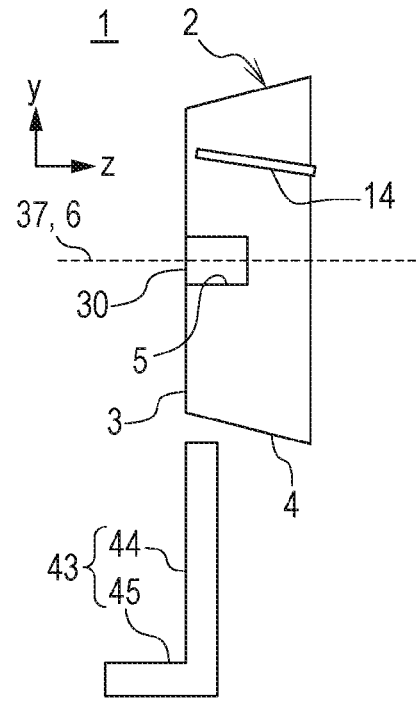
[Fig. 6B]
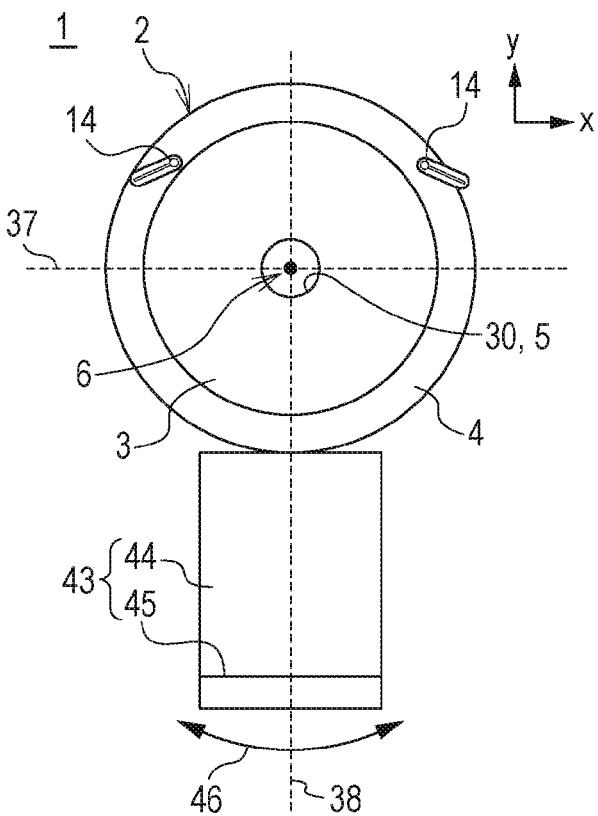

[Fig. 6C]
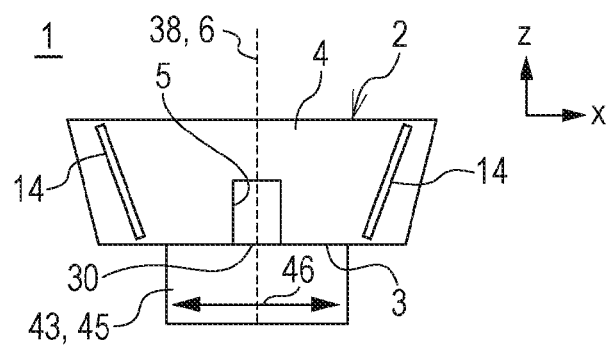
[Fig. 6D]
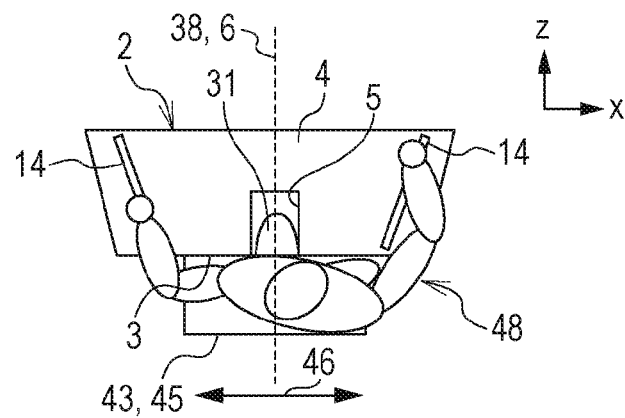

[Fig. 7A]
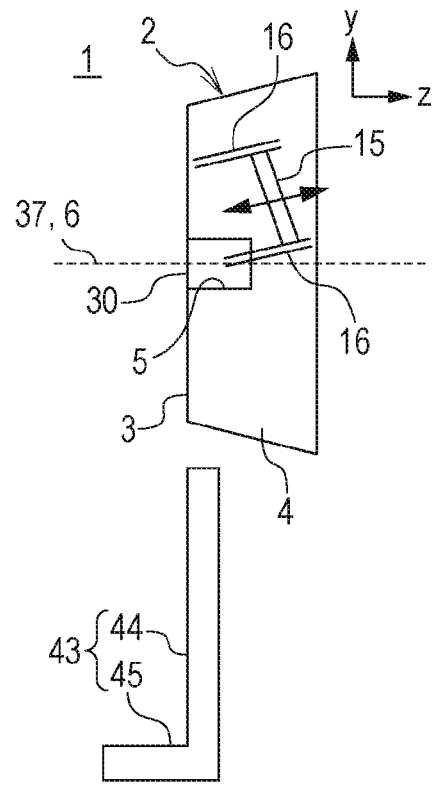
[Fig. 7B]
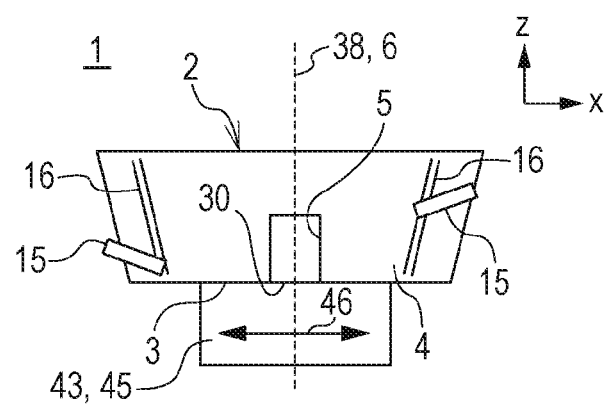

[Fig. 7C]
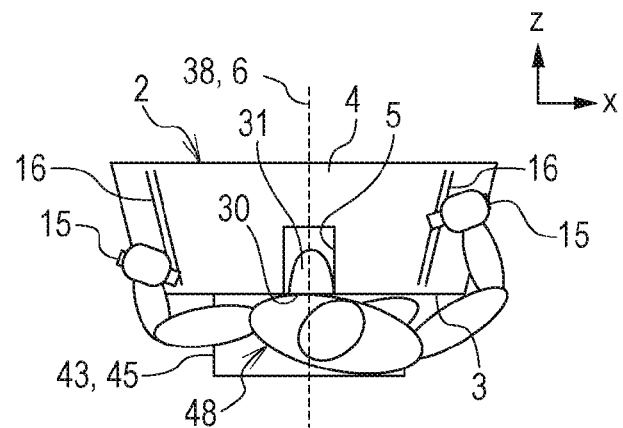
[Fig. 7D]
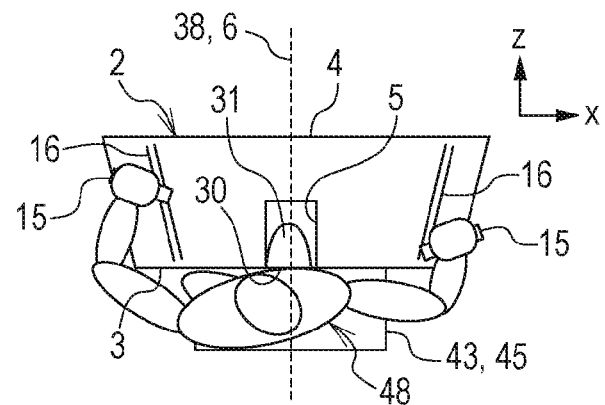

[Fig. 8A]
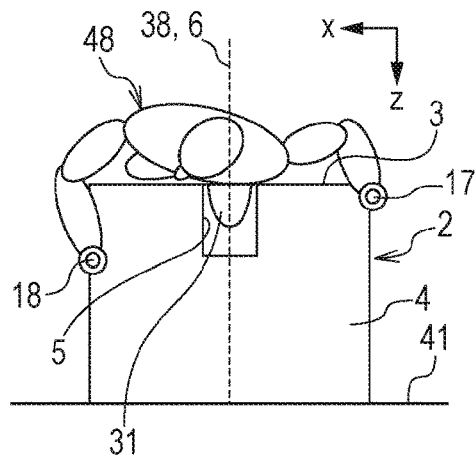
[Fig. 8B]
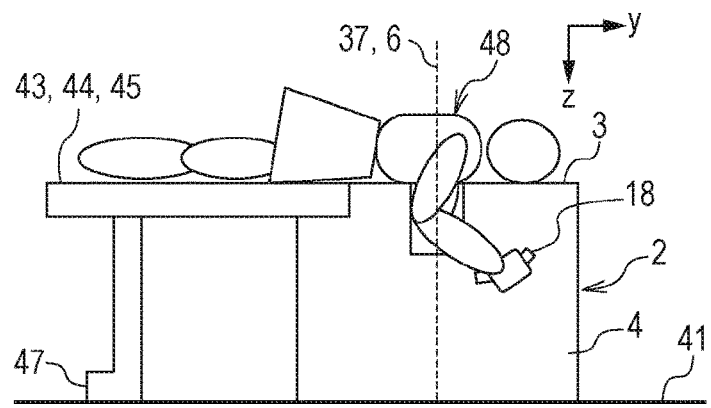
[Fig. 8C]
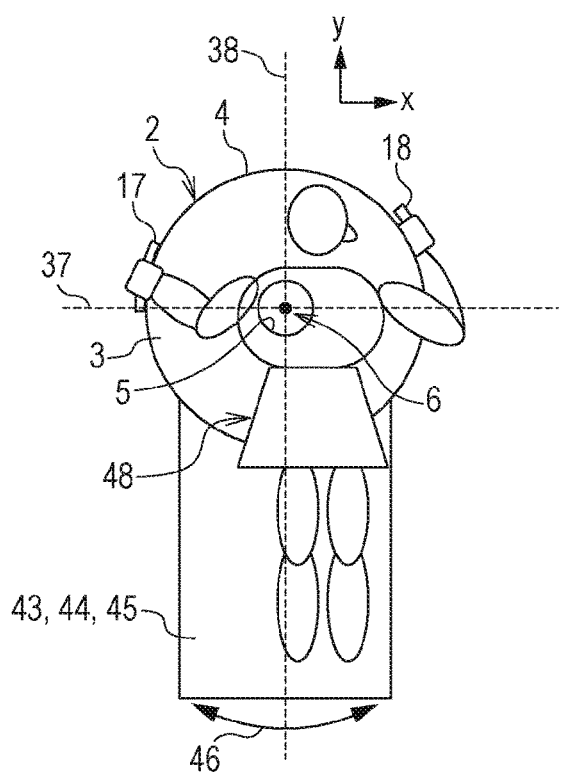

[Fig. 9A]
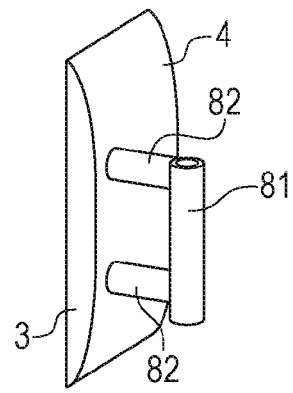
[Fig. 9B]
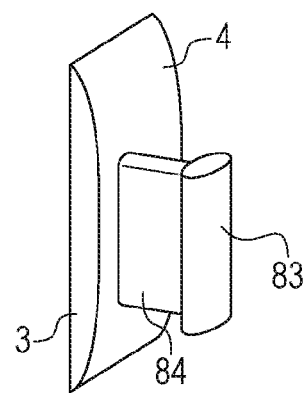
[Fig. 9C]
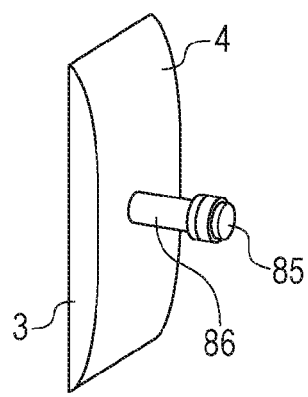
[Fig. 9D]
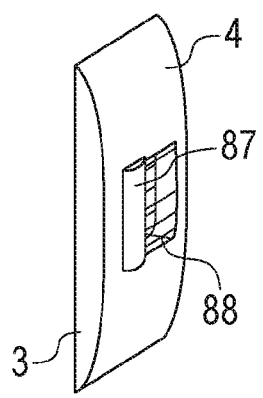

[Fig. 9E]
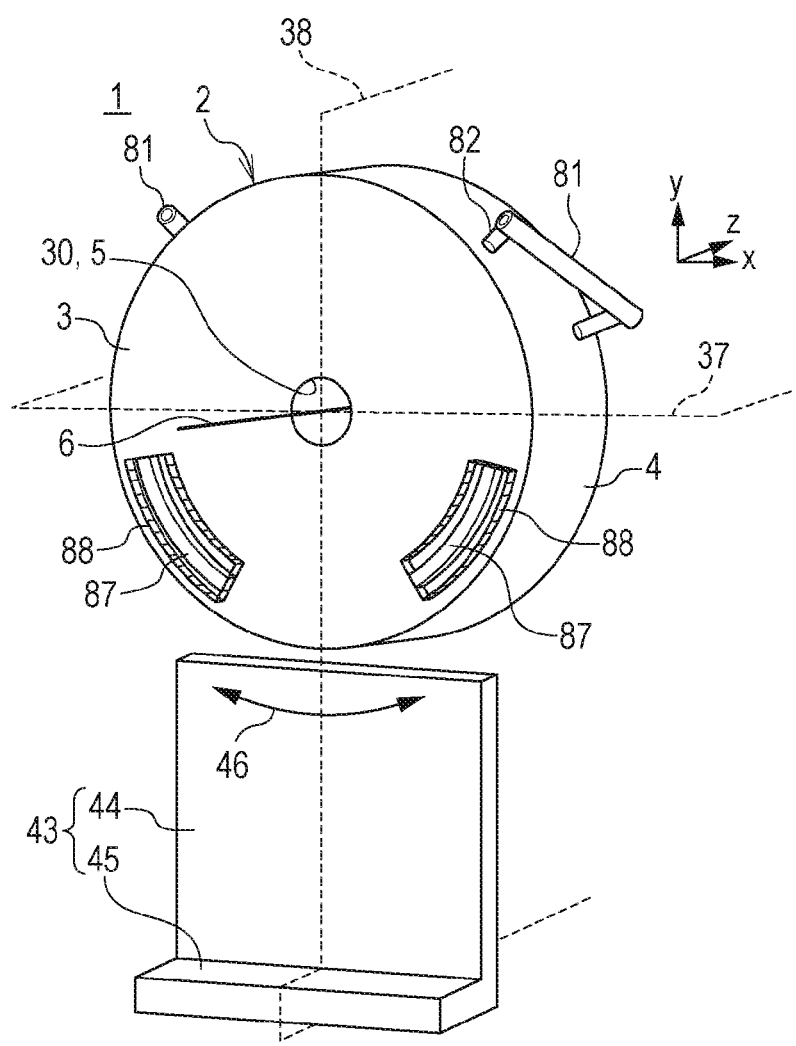

[Fig. 10A]
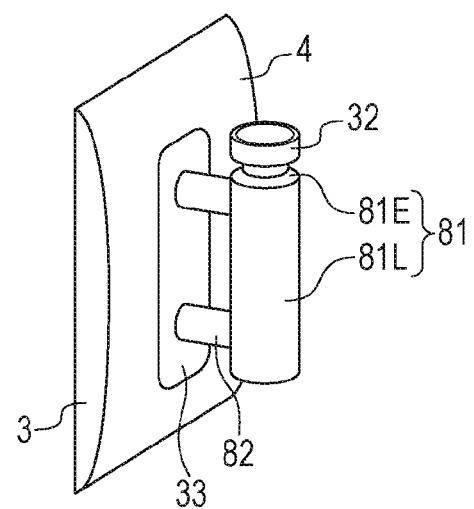

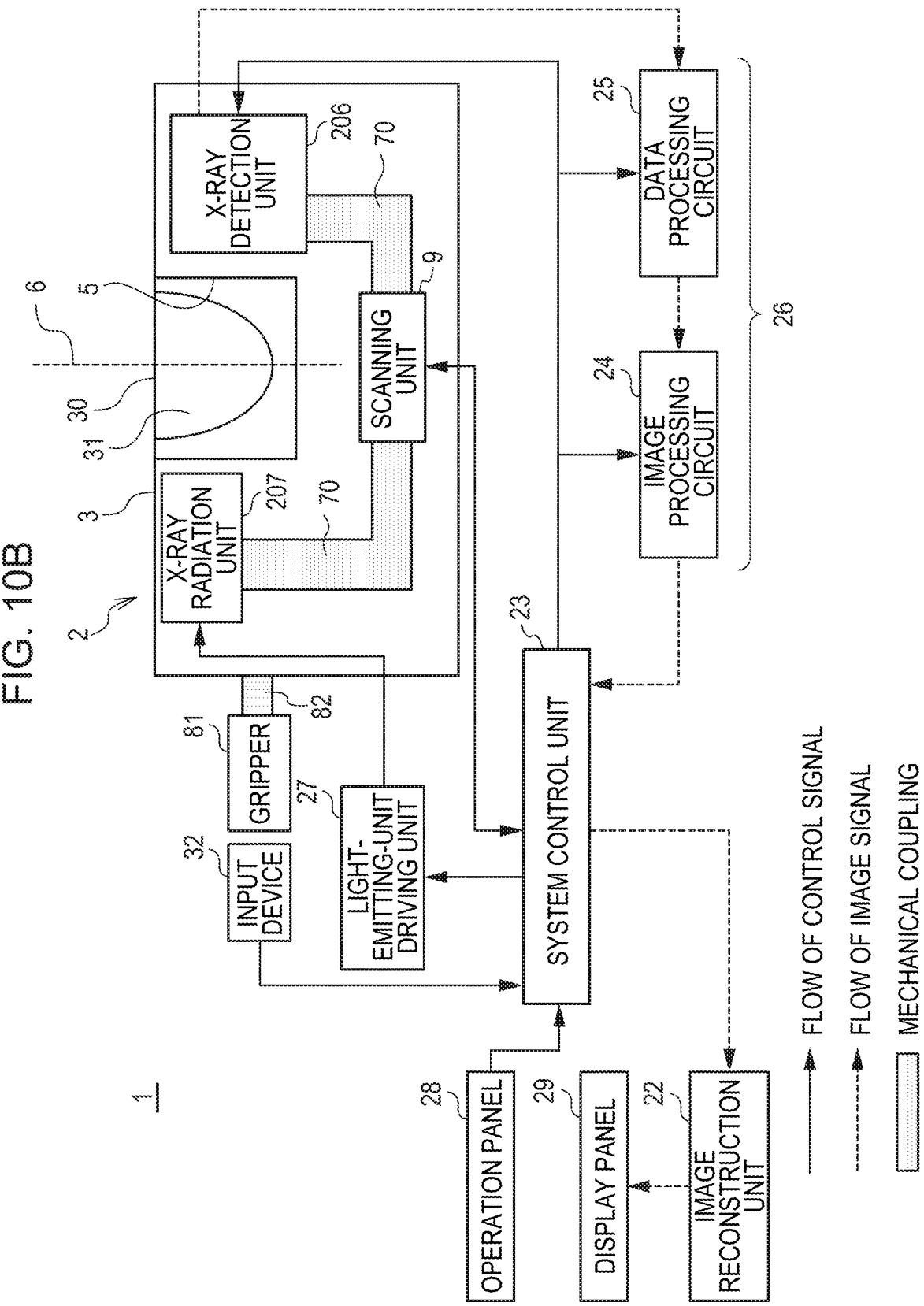

[Fig. 11A]
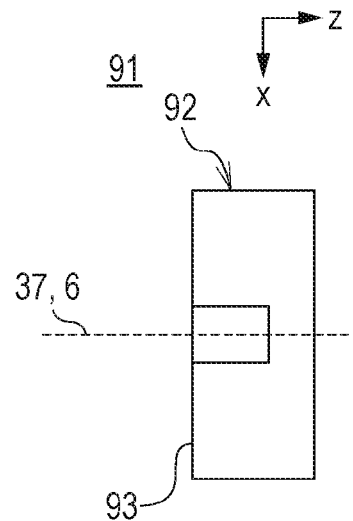
[Fig. 11B]
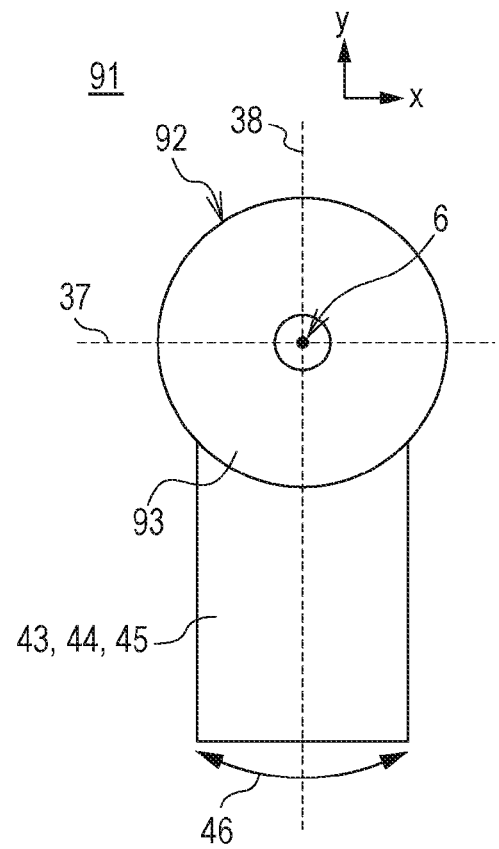

[Fig. 11C]
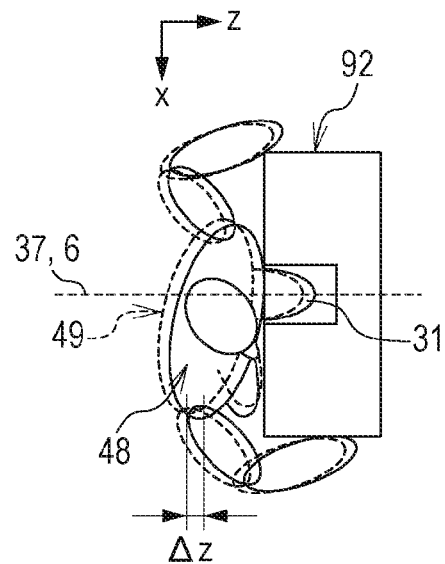
[Fig. 11D]
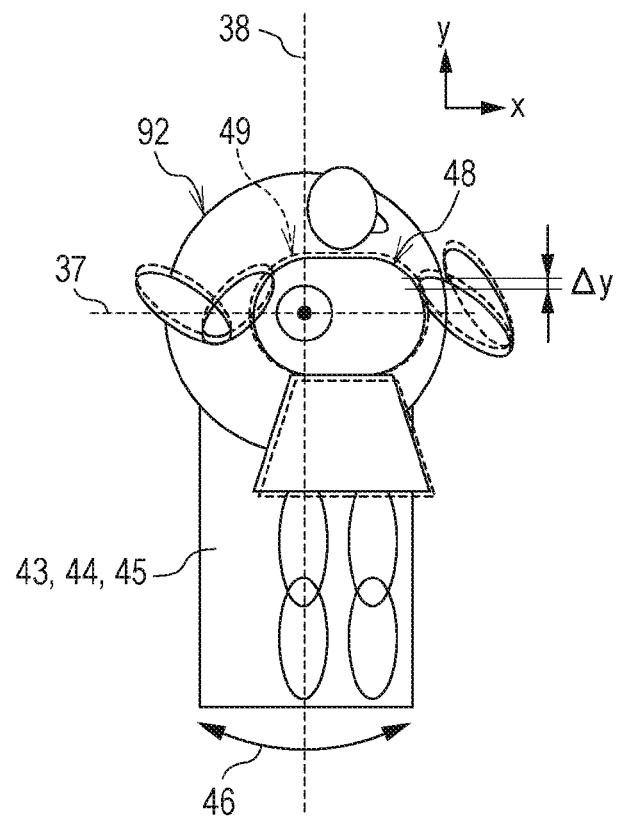

BREAST COMPUTED TOMOGRAPHY SYSTEM COMPRISING A GRIPPER

TECHNICAL FIELD

The present invention relates to a computed tomography system for the breast for acquiring tomographic images of the breast in the field of medical equipment.

BACKGROUND ART

Mammography apparatuses that capture X-ray images of the breast have recently been used to detect breast cancer. However, it is sometimes difficult to detect a tumor or a calcified region that overlaps with the tissue of, for example, mammary gland, because the images captured by the mammography apparatuses are flat images. This leads to development of a computed tomography system for the breast for capturing tomographic images of the breast using a computed tomography technique.

PTL 1 and PTL 2 disclose cone-beam breast computed tomography systems including an X-ray radiation unit and an X-ray detection unit. PTL 3 discloses a photoacoustic computed tomography system (PACT) for the breast including an infrared irradiation unit and an ultrasonic detection unit.

All of the computed tomography systems for the breast disclosed in PTLs 1 to 3 include a front plate disposed adjacent to the examinee and are configured to allow the breast of the examinee to be inserted into a breast insertion section communicating with an opening in the front plate.

CITATION LIST

Patent Literature

PTL 1: Japanese Patent Laid-Open No. 2008-307236
PTL 2: Japanese Patent Laid-Open No. 2010-69241
PTL 3: Japanese Patent Laid-Open No. 2014-23681

SUMMARY OF INVENTION

Technical Problem

The computed tomography systems for the breast disclosed in PTL 1 to PTL 3 capture tomographic images by scanning the light emitting unit, with at least one of the position of the light emitting unit relative to the breast and the optical axis of light applied to the breast changed in sequence. The scanning of the light emitting unit requires that the breast, or the subject, is at rest in the viewpoint of the quality of captured images. The scanning of the light emitting unit sometimes needs several tens of seconds to several minutes, although it depends on the voxel size of the tomographic images and the scan pitch.

As disclosed in PTL 2 and PTL 3, the known computed tomography systems for the breast use a front plate of the gantry as a bed upward oriented in the vertical direction for the purpose of keeping the breast at rest during image capturing or for the purpose of providing a large image capturing region of the breast. Such computed tomography systems for the breast are expected to have the effect of bringing the chest into close-contact with the front plate using the own weight of the upper half of the body of the examinee in a prone position. However, it is difficult for such computed tomography systems for the breast to effectively reduce the involuntary movement of the examinee, resulting in the possibility of reduction in the quality of the captured images due to the positional shift of the chest or the breast of the examinee.

As disclosed in PTL 1, the known breast computed tomography system sucks the breast in a breast insertion section for the purpose of keeping the breast at rest during image capturing and for the purpose of providing a large image capturing region of the breast. However, the suction of the breast can cause internal bleeding and pain due to pressure, decreasing the usability, thus making it difficult for the examinee to keep a fixed image capturing posture during the image capturing time.

The computed tomography system for the breast disclosed in PTL 2 includes an assistive device for pressing the back of the examinee for the purpose of keeping the breast at rest during image capturing or for the purpose of providing a large image capturing region of the breast. However, this breast computed tomography system requires the examinee to keep the body bent backward on an examination bed having a recess, decreasing the usability, thus making it difficult for the examinee to keep a fixed image capturing posture during the image capturing time.

The present invention provides a breast computed tomography system capable of capturing high-quality tomographic images of the breast by reducing the movement of the body of the examinee during image capturing without decreasing the usability.

Solution to Problem

The present invention provides a breast computed tomography system comprising:
a light emitting unit configured to emit light to a breast of an examinee;
a scanning unit configured to move the light emitting unit to different positions relative to the breast;
a detection unit configured to detect waves extracted from a region of the breast irradiated with the light;
a gantry accommodating the light emitting unit and the detection unit, the gantry including a front plate configured to being adjacent to the examinee;
a breast insertion section communicating with an opening in the front plate; and
a gripper secured to the gantry,
wherein the gripper includes a right gripping portion and a left gripping portion.

Advantageous Effects of Invention

According to embodiments of the present invention, positional changes of the breast, or subject, can be reduced without decreasing the usability, thus allowing capturing of high-quality tomographic images of the breast.

Further features of the present invention will become apparent from the following description of exemplary embodiments with reference to the attached drawings.

BRIEF DESCRIPTION OF DRAWINGS

FIG. 1A is a side view of a breast computed tomography system according to a first embodiment of the present invention.

FIG. 1B is a front view of the breast computed tomography system according to the first embodiment.

FIG. 1C is a top view of the breast computed tomography system according to the first embodiment.

FIG. 1D is a top view of an image capturing posture during examination of the left breast according to the first embodiment.

FIG. 1E is an elevation view of the image capturing posture during examination of the left breast according to the first embodiment.

FIG. 2B is a schematic configuration diagram of the breast computed tomography system according to the second embodiment.

FIG. 2C is a schematic configuration diagram of a breast computed tomography system according to a third embodiment of the present invention.

FIG. 3 is a flowchart for the image capturing operation of the breast computed tomography system according to the second embodiment.

FIG. 4A is a diagram illustrating an image capturing posture for the left breast in the breast computed tomography system according to the first embodiment.

FIG. 4B is a diagram illustrating an image capturing posture for the right breast in the breast computed tomography system according to the first embodiment.

FIG. 4C is a diagram illustrating an image capturing posture for the left breast in the breast computed tomography system according to the first embodiment.

FIG. 4D is a diagram illustrating an image capturing posture for the left breast in the breast computed tomography system according to the first embodiment.

FIG. 5A is a side view of a breast computed tomography system according to a fourth embodiment of the present invention.

FIG. 5B is a front view of the breast computed tomography system according to the fourth embodiment.

FIG. 5C is a top view of the breast computed tomography system according to the fourth embodiment.

FIG. 5D is a top view of an image capturing posture according to the fourth embodiment.

FIG. 5E is a schematic configuration diagram of a modification of the fourth embodiment including a posture changing unit.

FIG. 6A is a side view of a breast computed tomography system according to a fifth embodiment of the present invention.

FIG. 6B is a front view of the breast computed tomography system according to the fifth embodiment.

FIG. 6C is a top view of the breast computed tomography system according to the fifth embodiment.

FIG. 6D is a top view of an image capturing posture during examination of the left breast according to the fifth embodiment.

FIG. 7A is a side view of a breast computed tomography system according to a sixth embodiment of the present invention.

FIG. 7B is a top view of the breast computed tomography system according to the sixth embodiment.

FIG. 7C is a top view of an image capturing posture during examination of the left breast according to the sixth embodiment.

FIG. 7D is a top view of an image capturing posture during examination of the right breast according to the sixth embodiment.

FIG. 8A is a side view of an image capturing posture in a breast computed tomography system according to a seventh embodiment of the present invention.

FIG. 8B is a longitudinal side view of the image capturing posture in the breast computed tomography system according to the seventh embodiment.

FIG. 8C is a plan view of the image capturing posture in the breast computed tomography system according to the seventh embodiment.

FIG. 9A is a schematic configuration diagram illustrating a modification of a gripper.

FIG. 9B is a schematic configuration diagram illustrating another modification of a gripper.

FIG. 9C is a schematic configuration diagram illustrating a still another modification of a gripper.

FIG. 9D is a schematic configuration diagram illustrating a still another modification of a gripper.

FIG. 9E is a schematic configuration diagram of a breast computed tomography system according to an eighth embodiment of the present invention.

FIG. 10A is an enlarged view of a gripper of a breast computed tomography system according to a ninth embodiment of the present invention.

FIG. 10B is a block diagram of a breast computed tomography system according to the ninth embodiment.

FIG. 11A is a top view of a breast computed tomography system of a reference example.

FIG. 11B is an elevation view of the breast computed tomography system of the reference example.

FIG. 11C is a top view of an image capturing posture of an examinee in the breast computed tomography system of the reference example.

FIG. 11D is a plan view of the image capturing posture of the examinee in the breast computed tomography system of the reference example.

DESCRIPTION OF EMBODIMENTS

Figure 2A:
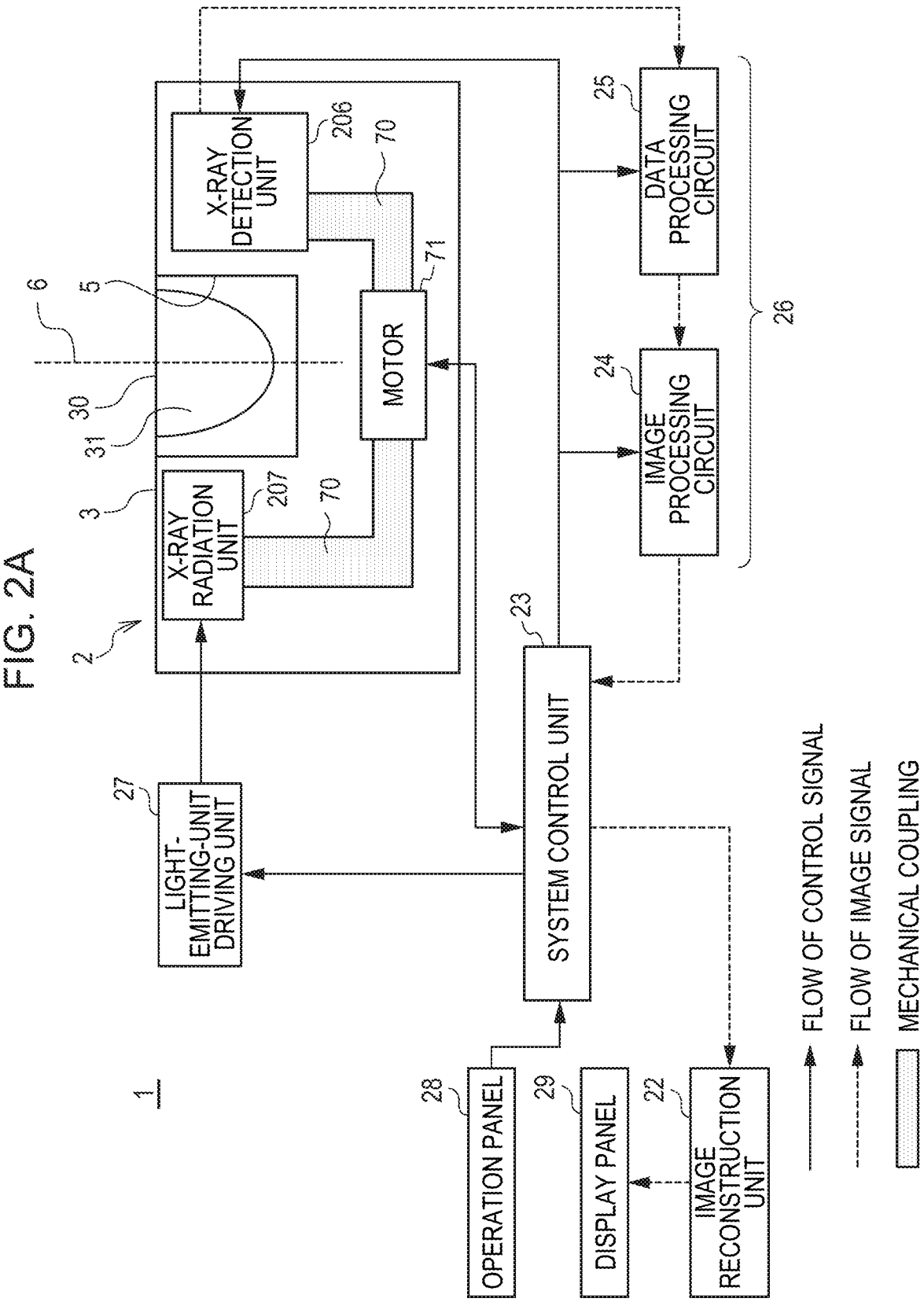
FIG. 2A is a block diagram of a breast computed tomography system according to a second embodiment of the present invention.

Computed tomography systems for the breast according to embodiments of the present invention will be described hereinbelow with reference to the drawings. Note that the materials, dimensions, shapes, and relative positions of the components described in the embodiments are given for mere illustration and are not intended to limit the scope of the present invention unless otherwise noted.

Referring to FIGS. 1A to 1E to FIGS. 10A and 10B, computed tomography systems for the breast according to embodiments of the present invention will be described.

Computed Tomography System for Breast

An X-ray tomography system that incorporates a breast computed tomography system according to an embodiment of the present invention will be described with reference to FIGS. 2A and 2B and FIG. 3.

FIG. 2B illustrates the schematic configuration of a breast computed tomography system 1 according to a second embodiment applied to a mammography X-ray CT system. FIG. 2B differs from FIG. 2A in that FIG. 2B illustrates components disposed in a gantry 2.

The breast computed tomography system 1 according to the second embodiment is a cone-beam X-ray CT system for capturing tomographic images of a breast 31 by radiating cone-shaped X-ray beams onto the breast 31 while rotating. The breast computed tomography system 1 of this embodiment includes a gantry 2 and a leg mount 43 so that an examinee 48 can take a prone posture.

The gantry 2 has a front plate 3 having an opening communicating with a breast insertion section 5 into which the breast 31 can be inserted at the examinee 48 side. The gantry 2 accommodates an X-ray radiation unit 207 that radiates cone-shaped X-ray beams toward the breast insertion section 5, an X-ray detection unit 206 that detects X-rays that have passed through the breast 31, and a scanning unit 9 including a rotation base 70 and a motor 71.

The gantry 2 accommodates the X-ray radiation unit 207 for radiating an X-ray beam 208 necessary for image capturing. The X-ray radiation unit 207 corresponds to a X-ray radiation window of an X-ray generating tube 407. Accordingly, a tube voltage circuit for driving the X-ray generating tube 407, a blanking circuit, and a focusing lens (not shown) may be disposed either in or outside the gantry 2.

The X-ray radiation unit 207 and the X-ray detection unit 206 are connected to the motor 71 via the rotation base 70 and are opposed to each other with the breast insertion section 5 therebetween. The X-ray radiation unit 207 and the X-ray detection unit 206 rotate along a plane parallel to the front plate 3 while drawing a scanning trajectory 209 with the rotational scanning with the scanning unit 9.

The gantry 2 serves both as a container that accommodates the X-ray radiation unit 207 (a light emitting unit), the scanning unit 9, and the X-ray detection unit 206 (a detection unit) and a user interface in contact with the examinee 48 and having a gripper (described later), which is a feature of the present invention.

The central axis 6 is disposed so as to pass through substantially the center of the breast insertion section 5 and to be perpendicular to the front plate 3 for the purpose of reducing the blind area of the breast 31 adjacent to the rib cage. This disposition allows the X-ray radiation unit 207 to rotationally scan in the vicinity of the front plate 3, reducing the blind area. The X-ray radiation unit 207, or the light emitting unit, emits the X-ray beam 208 whose intensity repeatedly changes with scanning for the purpose of reducing image blurs included in the X-ray images (original images) detected by the X-ray detection unit 206. The X-ray generating tube 407 according to this embodiment is pulse-driven by the blanking operation of an electron emission source (not shown).

The rotation base 70 and the motor 71 that are mechanically coupled to the X-ray radiation unit 207 and the X-ray detection unit 206 of this embodiment are collectively referred to as a scanning unit 9 of the breast computed tomography system 1. The scanning unit 9 corresponds to a unit that changes in direction and position in the process of scanning for capturing a plurality of two-dimensional images, which are original images that form tomographic images. Accordingly, the scanning unit 9 is also referred to as a mechanism for changing the position and direction of the X-ray radiation unit 207 relative to the breast 31.

The X-ray detection unit 206 has a plurality of X-ray detecting elements arranged to form an array unit (not shown) for detecting the intensity of X-rays. The waves that the X-ray detection unit 206 detects are X-rays that have transmitted through the breast 31. The transmitted X-rays include biological characteristic information based on the X-ray attenuation ratio of the breast 31.

Referring next to FIG. 2A, a control mechanism for image capturing manner of the X-ray CT system incorporating the breast computed tomography system 1 according to an embodiment of the present invention will be described. FIG. 2A illustrates the basic configuration example of the breast computed tomography system 1 that captures a plurality of transmitted X-ray images of the breast 31 at different angles about the central axis 6 to capture X-ray tomographic images.

The X-ray radiation unit 207 radiates pulsed X-rays whose output intensity is repeatedly changed by a light-emitting-unit driving unit 27 under the instruction of a system control unit 23. The output of the X-ray detection unit 206 includes data on transmitted X-ray images and is connected to a display panel 29 via a data processing circuit 25, an image processing circuit 24, a system control unit 23, and an image reconstruction unit 22. The data processing circuit 25 and the image processing circuit 24 constitute a signal processing unit 26, as illustrated in FIG. 2A.

The output of the system control unit 23 is connected to the light-emitting-unit driving unit 27, the X-ray radiation unit 207, the scanning unit 9, the data processing circuit 25, and the image processing circuit 24. The system control unit 23 receives the output of an operation panel 28.

The breast computed tomography system 1 of this embodiment is configured such that the X-ray radiation unit 207 and the X-ray detection unit 206 are opposed and rotate about the central axis 6 in synchronization so as to capture transmission images of the breast 31 at different angles.

The sequence of tomography with the rotational scanning of the X-ray radiation unit 207 in the breast computed tomography system 1 illustrated in FIG. 2A will be described with reference to FIG. 3.

FIG. 3 is a flowchart for the image capturing operation of the breast computed tomography system 1. When an instruction to start image capturing is input through the operation panel 28 (step S101), the X-ray radiation unit 207 and the X-ray detection unit 206 start to rotate at a predetermined rotational speed with the scanning unit 9 via the system control unit 23 (step S102). The system control unit 23 monitors encoder signals generated from the scanning unit 9 to determined whether at least one of the X-ray radiation unit 207 and the X-ray detection unit 206 has reached a predetermined speed and a predetermined angle.

When the predetermined speed and angle have been reached, the system control unit 23 transmits a signal to the X-ray radiation unit 207 via the light-emitting-unit driving unit 27 to start radiation of X-rays (step S103) to the breast 31. At the same time, the X-ray detection unit 206 collects image data via the data processing circuit 25 (step S104).

The image capturing is continued until a predetermined number of pieces of image data are collected with the synchronous rotation of the X-ray radiation unit 207 and the X-ray detection unit 206 at predetermined rotation angles. Upon completion of collection of image data captured at individual predetermined angles, the synchronous rotation of the X-ray radiation unit 207 and the X-ray detection unit 206 is terminated (step S105).

Next, the image reconstruction unit 22 reconstructs the image data into two-systems of reconstructed image data. The reconstruction is such that first reconstructed image data is constructed on the basis of electrical signals output from a high-resolution region detected by the X-ray detection unit 206, and second reconstructed image data is reconstructed on the basis of electrical signals output from a low-resolution region (step S106).

Next, corresponding first reconstructed image data and second reconstructed image data are combined at a given ratio. Specifically, the first reconstructed image data is multiplied by a coefficient k1, and the second reconstructed image data is multiplied by a coefficient k2. The two resultant pieces of image data are added together (step S107).

Thus, tomographic images are acquired from the plurality of X-ray transmission images of the breast 31 and angular information. In many cases, the time taken for the scanning process (step S102 to S104), which depends on the settings of the resolution, voxel, signal-to-noise ratio, and so on of the tomographic images, is set to several tens of seconds to several minutes, which is generally sufficiently longer than the period of breathing or heartbeat of the examinee 48.

The breast computed tomography system 1 according to an embodiment of the present invention is not necessarily limited to the X-ray CT system provided that it includes the gantry 2 that accommodates the scanning unit 9 that moves the X-ray radiation unit 207 relative to the breast 31 and that the examinee 48 is required to keep an image capturing posture throughout image capturing.

FIG. 2C illustrates a breast computed tomography system 1 according to a third embodiment of the present invention applied to a photoacoustic breast computed tomography system. The third embodiment differs from the second embodiment in the components disposed in the gantry 2.

This embodiment includes an infrared irradiation unit 307 serving as a light emitting unit, a liquid tank 74, an ultrasonic detection unit 306 serving as a detection unit, and a scanning unit 9 including an X-Y stage 75 that moves the infrared irradiation unit 307 relative to the breast 31.

As in the second embodiment, the gantry 2 of the third embodiment accommodates the infrared irradiation unit 307 for irradiating the breast 31 with infrared rays necessary for image capturing. If a light-source unit including an optical path unit including an optical fiber and a diffusing lens and a laser source is used (not shown), the infrared irradiation unit 307 corresponds to an emission end of the optical fiber. Accordingly, the laser source may be disposed either in or outside the gantry 2. The infrared irradiation unit 307 intermittently radiates infrared rays 308 to the breast 31 to cause a predetermined local region in the breast 31 to absorb the infrared rays to cause a pressure change in the region due to thermal expansion and thermal contraction, thereby causing the local region to generate elastic waves. The radiated light in this embodiment includes near-infrared rays and mid-infrared rays with wavelengths ranging from 0.7 µm to 4.0 µm, and preferably, near-infrared rays with wavelengths from 0.7 µm to 2.5 µm.

The liquid tank 74 is a container that contains an acoustic-impedance matching member for matching the acoustic impedance of the path from the infrared irradiation unit 307 to the ultrasonic detection unit 306 to transmit the elastic waves generated in the breast 31 as photoacoustic waves to the periphery. In this embodiment, the acoustic-impedance matching member is water, and the liquid tank 74 is a water tank.

The ultrasonic detection unit 306 is an ultrasonic detection unit that detects the photoacoustic waves that have reached from the breast 31 via the acoustic-impedance matching member and that has detection sensitivity in the ultrasonic band from 100 kHz to 10 MHz. The ultrasonic detection unit 306 may be a plurality of probes arrayed in a flat plane or a curved plane.

The initial sound pressure $P_0$ of photoacoustic waves generated from an absorber due to light absorption in image capturing using photoacoustic waves, that is, photoacoustic imaging, can be expressed as the following equation:

$$P_0 = \Gamma \times \mu_a \times \Phi \quad (1)$$

where $\Gamma$ is a Grueneisen constant, which is obtained by dividing the product of a thermal expansion coefficient $\beta$ and the square of the velocity of sound c by a specific heat under constant pressure $C_P$, $\mu_a$ is the optical absorption coefficient of the absorber, and $\Phi$ is the amount (fluence) of light applied to the absorber. Measuring and analyzing the changes of the pressure of sound, P, which is the magnitude of acoustic waves, at a plurality of positions gives the product of $\Gamma$, $\mu_a$, and $\Phi$, that is, information on a Grueneisen constant distribution and an optical-absorption-energy-density distribution.

In other words, the photoacoustic waves detected by the ultrasonic detection unit 306 include biological information based on the Grueneisen constant $\Gamma$ and the optical absorption coefficient $\mu_a$ related to thermal expansion coefficient $\beta$ and the specific heat under constant pressure $C_p$.

The X-Y stage 75 moves the infrared irradiation unit 307 relative to the breast 31 to allow a predetermined region of the breast 31 to locally generate elastic waves. The X-Y stage 75 of this embodiment is configured to cause the infrared irradiation unit 307 and the ultrasonic detection unit 306 to spirally scan together while drawing a scanning trajectory 309. The scanning of the infrared irradiation unit 307 include not only the spiral scanning but also any scanning in which the region of the breast 31 irradiated with infrared rays from the infrared irradiation unit 307 is changed, for example, rotational scanning, precessional scanning, horizontal zigzag scanning, and raster scanning.

Also in the third embodiment illustrated in FIG. 2C, the examinee 48 is required to keep a posture in which the body is in close-contact with the front plate 3 of the gantry 2 during the scanning process in the viewpoint of reducing the blurs of the object among images to reduce artifacts due to the blur of the object.

Gantry

The gantry 2 provided with a gripper unit 11, which is a feature of the present invention, will next be described with reference to FIGS. 1A to 1E, FIGS. 2A to 2C, and FIGS. 8A to 8C.

FIGS. 1A to 1C illustrate the breast computed tomography system 1 in which the gantry 2 is disposed in such a manner that the front plate 3 is parallel to the vertical direction (the y-direction) and that the central axis 6 (the z-direction) is in the horizontal direction so that the examinee 48 can take an erected position in FIGS. 1A and 1B. In this specification, a state in which the front plate 3 is disposed in the vertical direction as in FIGS. 1A to 1C is referred to as an erect position of the gantry 2. In contrast, a state in which the front plate 3 is disposed in such a manner that a normal to the front plate 3 is directed upward as in FIGS. 2B and 2C is referred to as a horizontal position of the gantry 2.

The drawings in the embodiments illustrate the reference vectors of x-y-z rectangular coordinates as required for the purpose of illustrating the position of the gripper relative to the gantry 2 and the image capturing posture of the examinee 48. Specifically, as illustrated in FIGS. 1D and 1E, the y-axis is defined along the body axis of the examinee 48, the x-axis is defined in the lateral direction of the examinee 48, and the z-axis is defined in a direction in which the examinee 48 faces the gantry 2. The breast insertion section 5 of the gantry 2 and the body axis of the examinee 48 are oriented so that the image capturing posture of the examinee 48 is fixed when the examinee 48 faces in contact with the gantry 2.

The gantry 2 of the embodiments includes the front plate 3, an opening 30 in the front plate 3, the breast insertion section 5 into which the breast 31 can be inserted through the opening 30, and a side surface 4 connecting to the edge of the front plate 3 and surrounding a scanning unit (not shown). The breast insertion section 5 has a central axis 6 perpendicular to the front plate 3 and passing through the center of the opening 30. The disposition of the front plate 3 and the central axis 6 in perpendicular relationship has the effect of ensuring symmetry about the central axis 6 and reducing the blind area of the breast 31.

The breast computed tomography system 1 of the embodiments includes a leg mount 43, next to the front plate 3, for the lower half of the examinee 48, in particular, the legs. The leg mount 43 is disposed next to the front plate 3 so as to stabilize the upper half and the lower half of the examinee 48 relative to the gantry 2. When the gantry 2 is in the horizontal position, as illustrated in FIGS. 2B and 2C, the leg mount 43 constitutes an examination bed together with the front plate 3 to allow the examinee 48 to take an image capturing posture in a prone position. Thus, the leg mount 43 is a user interface of the examinee 48, like the front plate 3, or serves as part of the front plate 3.

The leg mount 43 of the embodiments is disposed below the opening 30 in the vertical direction in such a manner that the center of the leg mount 43 aligns with the center of the opening 30. In other words, a vertical plane 38 including the central axis 6 in the embodiments passes through the leg mount 43 and passes through, particularly, the center of the leg mount 43 in a circumferential direction 46 of the gantry 2 about the central axis 6.

The leg mount 43 includes a leg mount region 44 on which at least any of the thighs, lower legs, and knees of the examinee 48 are placed and a feet mount region 45 on which the feet are placed. The leg mount 43 is provided to stabilize the upper half and the lower half of the examinee 48 relative to the gantry 2. At least part of the leg mount 43 may serve also as an installation surface (not shown) on which the breast computed tomography system 1 is installed.

As illustrated in FIGS. 1A to 1E, the gantry 2 is defined by a top-bottom segmenting plane 37 and the vertical plane 38 including the central axis 6, which divide the gantry 2 into four upper, lower, right, and left segments with reference to the breast insertion section 5 in terms of relationship with the examinee 48. The upper and lower segments correspond respectively to the upper one fourth and the lower three fourths of the examinee 48 with respect to the breast 31 in the direction of the body axis along the height of the examinee 48, and the right and left segments correspond respectively to the right arm and the left arm of the examinee 48.

When the gantry 2 is at a position at which the front plate 3 is not in the horizontal position, as illustrated in FIGS. 1A to 1C and FIG. 5E, the top-bottom segmenting plane 37 (an X-Z plane) is an imaginary plane defined to include the central axis 6 (the Z-direction) and to cross the vertical direction. Similarly, when the gantry 2 is at a position at which the front plate 3 is not in the horizontal direction, as illustrated in 1A to 1C and FIG. 5E, the vertical plane 38 (the Y-Z plane) including the central axis 6 is an imaginary plane defined to include the central axis 6 (the Z-direction) and to be parallel to the vertical direction.

In contrast, when the gantry 2 is in the horizontal position at which the front plate 3 is in the horizontal direction, as illustrated in FIGS. 8A to 8C, the top-bottom segmenting plane 37 and the vertical plane 38 including the central axis 6 are defined by the direction of the body axis of the examinee 48 at the prone position.

The vertical plane 38 including the central axis 6 is defined by a plane that is parallel to a line connecting the center of the opening 30 and the center of the leg mount 43 and that passes through the central axis 6. In a typical examination bed, the gantry 2 and the leg mount 43 connect in the longitudinal direction along the body axis of the examinee 48 who is in a prone position. Therefore, the vertical plane 38 including the central axis 6 may be defined to be parallel to the longitudinal direction of the examination bed, thus providing universality.

Similarly, the top-bottom segmenting plane 37 is defined by a plane that is perpendicular to the line connecting the center of the opening 30 and the center of the leg mount 43 and that passes through the central axis 6. In a typical examination bed, the gantry 2 and the leg mount 43 connect in the longitudinal direction along the body axis of the examinee 48 who is in a prone position. Therefore, the top-bottom segmenting plane 37 may be defined to be perpendicular to the longitudinal direction of the examination bed, thus providing universality.

Gripper

Next, a gripper, which is a feature of the invention, will be described with reference to FIGS. 1A to 1E to FIGS. 10A to 10B.

As illustrated in FIGS. 1A to 1C, the gantry 2 according to a first embodiment includes a gripper unit 11 which is secured to the side surface 4 of the gantry 2 and is extending annularly across the vertical plane 38 including the central axis 6, for the examinee 48 to grip with both hands. The gripper unit 11 secured to the gantry 2 allows the examinee 48 to stably place the breast 31 in the breast insertion section 5 throughout the tomographic image capturing time in such a manner as to hold the gantry 2 with both arms (both hands), as illustrated in FIGS. 1D and 1E. This embodiment can reduce a decrease in usability because of fixation of the breast 31 under pressure or pressure on the back of the examinee 48 and can reduce changes in the position of the breast 31 throughout the tomographic image capturing time. FIGS. 1D and 1E illustrate only part of the gripper unit 11 that the examinee 48 grips, and the remaining part of the gripper unit 11 extending in the circumferential direction illustrated in FIGS. 1A to 1C is omitted for illustrative purpose.

FIGS. 11A and 11B illustrate a breast computed tomography system 91 in which a gantry 92 has no gripper as a reference example. The gantry 92 is disposed such that a front plate 93 is parallel to the vertical direction (the Y-direction).

The gantry 92 of this reference example includes no device for keeping the distance from the examinee 48. This makes it difficult to prevent the involuntary movement of the examinee 48 and to keep the breast 31 at rest throughout the tomographic image capturing time. Thus, in this reference example, the shoulders of the examinee 48 move both in a plane parallel to the front plate 3 and in the direction perpendicular to the front plate 3 during the image capturing time ($\Delta y$, $\Delta z$).

In this reference example, the gantry 92 takes an erect position. This makes it difficult to have the effect of pushing the body of the examinee 48 against the front plate 93 using the own weight of the examinee 48, as illustrated in FIGS. 11C and 11D. Thus, the breast computed tomography system 91 in which the gantry 92 has no gripper as in this reference example is more prone to be influenced by the body motion of the examinee 48 (indicated by dotted lines 49) due to breathing and heartbeat during image capturing than a case in which the gantry 92 is disposed in the horizontal position.

The body motion 49 occurs especially at the upper half of the examinee 48 having circulatory organs. Therefore, the shoulders of the examinee 48 may be fixed to the gantry 92 to reduce the body motion 49 of the examinee 48, but this is not desirable in the viewpoint of usability.

Another feature of the breast computed tomography system 1 according to the first embodiment will be described with reference to FIGS. 1A to 1E, FIGS. 2A and 2B, and FIGS. 4A to 4D.

As illustrated in FIG. 1B, this embodiment includes the ring-shaped gripper unit 11 extending in the circumferential direction over the vertical plane 38 including the central axis 6. In other words, the ring-shaped gripper unit 11 includes a right gripping portion 12 (13) and a left gripping portion 13 (12), which are located on one side and the other side of the vertical plane 38. The vertical plane 38 includes the central axis 6 perpendicular to the front plate 3 and passing through the center of the opening 30. The right gripping portion 12 (13) and the left gripping portion 13 (12) are located outwardly with respect to the opening 30 having a width $\Phi_H$ in the horizontal direction. In other words, the right gripping portion 12 (13) is located at the right side with respect to the opening 30 in a direction perpendicular to the vertical plane 38. The left gripping portion 13 (12) is located at the left side with respect to the opening 30 in the direction perpendicular to the vertical plane 38. Since the gripper unit 11 is disposed on both sides of the opening 30 width $\Phi_H$ in the horizontal direction, the examinee 48 can continue the image capturing posture in which the upper half is pushed against the front plate 3 with balance on both sides of the breast insertion section 5, as illustrated in FIGS. 4A and 4B.

As illustrated in FIGS. 2B and 2C, the gantry 2 has a side surface 4 connecting to the front plate 3 and surrounding the scanning range of the X-ray radiation unit 207 or infrared irradiation unit 307. The gripper unit 11 is disposed on the side surface 4 of the gantry 2, as illustrated in FIGS. 1A to 1E. The gripper unit 11 may be disposed on the front plate 3 of the gantry 2 or a back plate (not shown) opposed to the front plate 3. An embodiment in which the gripper unit 11 are disposed on the front plate 3 will be described later.

The breast computed tomography system 1 according to the first embodiment includes a ring-shaped front gripper 12 and a ring-shaped rear gripper 13. The front gripper 12 corresponds to a gripper unit 11 nearer to the front plate 3 than the rear gripper 13. The distance between the front gripper 12 and the front plate 3 and the distance between the rear gripper 13 and the front plate 3 differ in the z-direction in FIGS. 1A and 1C.

FIGS. 4A and 4B respectively illustrate the left and right image capturing postures of the examinee 48 during left and right image capturing in the breast computed tomography system 1 of the first embodiment. Disposing the front gripper 12 and the rear gripper 13 on both sides of the vertical plane 38 including the central axis 6, as in this embodiment, allows the examinee 48 to grip the gripper unit 11 at positions at different distances from the front plate 3.

In other words, as illustrated in FIG. 4A, the rear gripper 13, which is gripped with the right arm in a posture of the examinee 48 during image capturing of the left breast 31, is more distant from the front plate 3 on the gantry 2 than the front gripper 12, which is gripped with the left arm. In contrast, as illustrated in FIG. 49, the rear gripper 13, which is gripped with the left arm in a posture of the examinee 48 during image capturing of the right breast 31, is disposed on the gantry 2 more distant from the front plate 3 than the front gripper 12, which is gripped with the right arm. This allows the examinee 48 to stably keep the upper half in close-contact with the front plate 3 during image capturing of either of the right and left breasts 31, thereby preventing motion blur during image capturing of either of the right and left breasts 31.

For example, in an embodiment (not shown) having only the front gripper 12 of the first embodiment, the examinee 48 has to grip the front gripper 12, with one of both arms uneasily bent and the other extended. This can lead to a difference in contact between the shoulders and the front plate 3. The first embodiment illustrated in FIGS. 1A to 1E and FIGS. 4A to 4D has the effect of reducing the asymmetry in the close-contact of the shoulders of the examinee 48.

In this embodiment, as illustrated in FIGS. 1A to 1C, the front gripper 12 is nearer to the central axis 6 than the rear gripper 13. This disposition allows the examinee 48 to grip the remote rear gripper 13 without being obstructed by the front gripper 12 nearer to the examinee 48, as illustrated in FIG. 4C, allowing the examinee 48 to take a stable image capturing posture throughout the image capturing time.

Furthermore, in this embodiment, the side surface 4 expands in a direction away from the central axis 6 with increasing distance from the front plate 3, as illustrated in FIGS. 1A to 1C. This allows the examinee 48 to take an image capturing posture in which the upper arms are placed along the side surface 4, as illustrated in FIG. 1D. In other words, the side surface 4 of the gantry 2 of this embodiment serves as an arm rest. This allows the examinee 48 to take a further stable image capturing posture throughout the image capturing time.

Furthermore, as illustrated in FIGS. 1A and 1B, the gripper unit 11 of this embodiment has upper and lower portions on both sides of the top-bottom segmenting plane 37 that segments the examinee 48 into a head side and a leg side. The top-bottom segmenting plane 37 is a plane including the central axis 6 and perpendicular to the vertical plane 38 including the central axis 6.

This disposition allows the examinee 48 to take an image capturing posture in which the breast insertion section 5 is disposed between the right and left arms, as illustrated in FIG. 4D. This allows the upper half of the examinee 48 to keep in close-contact with both of the upper and lower portions of the front plate 3, with the breast insertion section 53 therebetween, allowing the image capturing posture to be further stable.

Next, a fourth embodiment will be described with reference to FIGS. 5A to 5E. FIGS. 5A to 5C are third angle projections of the fourth embodiment. FIG. 5D is a top view of an image capturing posture in the fourth embodiment. FIG. 5E is a diagram illustrating a modification of the fourth embodiment including a posture changing unit 62.

This embodiment differs from the first embodiment in that it includes a gripper unit 11 inclined with respect to the front plate 3 and that the gripper unit 11 includes a plurality of front grippers 12 and rear grippers 13 inclined at different angles with respect to the front plate 3.

Each of the front grippers 12 and the rear grippers 13 constituting the gripper unit 11 of this embodiment extends to a certain length in a direction crossing the front plate 3, as illustrated in FIGS. SA to 5C. In other words, the gripper unit 11 of this embodiment includes the front gripper 12 and the rear gripper 13 at different distances from the front plate 3 (in the z-direction) and at different positions in the vertical direction (the y-direction). The certain length of each gripper unit 11 in the direction crossing the front plate 3 is longer than the sum of the difference between the right and left breasts 31 of the examinee 48 and the width of the palm of the examinee 48, preferably, 120 mm to 1,000 mm.

This configuration allows the examinee 48 to grip the gripping units 11 at portions at different distances from the front plate 3 (corresponding to the front gripper 12 and the rear gripper 13) at different heights of the side surface 4 of the gantry 2, as illustrated in FIG. 5D. This allows the examinee 48 to grip the gripper unit 11 (the rear gripper 13) distant from the examinee 48 without being obstructed by the gripper unit 11 (the front gripper 12) nearer to the examinee 48, allowing a stable image capturing posture, as illustrated in FIG. 5D.

As illustrated in FIGS. 5A and 5C, the gripper unit 11 of this embodiment includes a proximal portion nearer to the front plate 3 and a distal portion farther from the front plate 3 than the proximal portion. The proximal portion is inclined at a larger angle with respect to the front plate 3 than the angle of the distal portion. In other words, the front gripper 12 nearer to the front plate 3 has a larger inclination angle with respect to the front plate 3 than the inclination angle of the rear gripper 13 farther from the front plate 3.

The examinee 48 takes an image capturing posture in which one arm that grips the front gripper 12 close to the examinee 48 is bent and the other arm that grips the rear gripper 13 far from the examinee 48 is stretched. The distributed inclination angles of the gripper unit 11 as in this embodiment allow the examinee 48 to grip the front gripper 12 close to the examinee 48 and the rear gripper 13 far from the examinee 48 without straining the wrists of the arms. This can further stabilize the image capturing posture of the examinee 48.

The modification of the fourth embodiment illustrated in FIG. 5E includes the posture changing unit 62 that tilts the breast computed tomography system 1 according to the fourth embodiment along the vertical plane 38 including the central axis 6. FIG. 5E illustrates a state in which the gantry 2 and the leg mount 43 of the fourth embodiment illustrated in FIG. 5A are tilted together through an angle of 36 degrees using the posture changing unit 62.

The posture changing unit 62 of this embodiment includes a joint support 63 connected to the gantry 2 and the leg mount 43, a rotating portion 64 connected to the joint support 63, for tilting the gantry 2 and the leg mount 43 together with the joint support 63, and a base 65 installed on an installation floor 41.

The posture changing unit 62 is configured to hold the relative positional relationship between the front plate 3 and the leg mount region 44. The joint support 63 is configured to change the distance between the front plate 3 and the leg mount 43 in a plane parallel to the vertical plane 38 including the central axis 6.

If the pressure of the examinee 48 who grips the gripper unit 11 against the front plate 3 is insufficient, the posture changing unit 62 brings the image capturing posture of the examinee 48 close to a lying position, thereby enhancing the contact between the examinee 48 and the front plate 3 due to the own weight.

Next, a fifth embodiment will be described with reference to FIGS. 6A to 6D. FIGS. 6A to 6C are third angle projections of the fifth embodiment, and FIG. 6D is a top view of an image capturing posture in the fifth embodiment.

This embodiment is the same as the first embodiment in that the gantry 2 has a side surface 4 that increases in distance from the central axis 6 with increasing distance from the front plate 3 but differs from the first and fourth embodiments in that the gantry 2 has a pair of grippers 14, along the side surface 4, which increases in distance from the central axis 6 with increasing distance from the front plate 3.

This allows the examinee 48 to grip the each of the pair of grippers 14 at positions at different distances from the front plate 3 on both sides of the vertical plane 38 including the central axis 6 with the arms stretched along the gripper 14 using the side surface 4 as an arm rest to stabilize the arms, as illustrated in FIG. 6D. Thus, this embodiment can reduce a burden on the examinee 48 and further stabilizes the image capturing posture throughout the image capturing time.

Next, a sixth embodiment will be described with reference to FIGS. 7A to 7D. FIGS. 7A and 7B are respectively a side view and a top view of the sixth embodiment. FIGS. 7C and 7D are respectively top views of image capturing postures during capturing of images of the left and right breasts 31 according to the sixth embodiment.

This embodiment differs from the first to fifth embodiments in that a breast computed tomography system 1 includes a connecting unit having a movable connecting portion 16. A gripped portion 15 is secured to the gantry 2 via the movable connecting portion 16 along which the gripped portion 15 can be moved and fixed at variable positions varied in a distance from the front plate 3 on both sides of the vertical plane 38 including the central axis 6. The movable connecting portion 16 includes a pair of parallel guide rails that allows the gripped portion 15 to slide along the side surface 4.

This embodiment allows the examinee 48 to take an image capturing posture in which the examinee 48 can grip the gripped portions 15 at positions suited to the physique, drawing force, gripping power, and so on of the examinee 48 on both sides of the vertical plane 38 including the central axis 6, as illustrated in FIGS. 7C and 7D. This configuration can reduce a burden on the examinee 48 and further stabilizes the image capturing posture throughout the image capturing time.

Next, a seventh embodiment will be described with reference to FIGS. 8A to 8C. FIGS. 8A to 8C are third angle projections of a posture in which images of the left breast 31 are captured in the seventh embodiment.

This embodiment differs from the first and the fourth to sixth embodiments and is the same as the second and third embodiments in that the front plate 3 of the gantry 2 us in a horizontal position to allow the examinee 48 to take an image capturing posture in a prone position. In this embodiment, grippers 17 and 18 are respectively disposed on the left and right sides of the examinee 48 with connecting units (not shown) detachable to any positions of the side surface 4 of the gantry 2. As in the sixth embodiment, the examinee 48 can take an image capturing posture in which the gripping positions are adjusted according the physique, physical condition, and so on of the examinee 48.

This embodiment allows the examinee 48 to take a stable image capturing posture for both of the left and right breasts 31 using the detachable grippers 17 and 18 even in a case where the body motion cannot be sufficiently prevented using the close-contact with the front plate 3 due to the own weight of the examinee 48 in a prone position.

Next, modifications of the gripper will be described with reference to FIGS. 9A to 9D. FIG. 9E is a perspective view of an eighth embodiment equipped with grippers of modifications.

The gripper of the present invention includes various modifications that allow the examinee 48 to take a stable image capturing posture with respect to the gantry 2. A rod-type gripper 81 illustrated in FIG. 9A is connected to the side surface 4 of the gantry 2 with a pair of connecting units 82. A rod-type gripper 83 illustrated in FIG. 9B is connected to the side surface 4 of the gantry 2 with a plate-like connecting unit 84. A bolt-head-like gripper 85 illustrated in FIG. 9C is connected to the side surface 4 of the gantry 2 with a columnar connecting unit 86.

A gripper 87 illustrated in FIG. 9D is a modification disposed along the side surface 4 of the gantry 2 in the circumferential direction together with a recess 88 in the side surface 4. Since this modification does not protrude from the gantry 2, this modification is suitable for a case in which a plurality of grippers 87 are disposed at positions of the side surface 4 at different distances from the front plate 3 or on the front plate 3.

FIG. 9E illustrates a breast computed tomography system 1 according to an eighth embodiment in which the grippers 87 and the recesses 88 are disposed on the front plate 3, and the grippers 81 and one pair of connecting units 82 are disposed on the both side surfaces 4, respectively. In this embodiment, the grippers 81 are disposed as head side gripping portions on the side surface 4 at an angle with respect to the front plate 3 so as to be at different distances from the front plate 3. The grippers 87 are disposed as leg side gripping portions, on the front plate 3, on both sides of the vertical plane 38 including the central axis 6 and at opposite positions from the grippers 81 with respect to the top-bottom segmenting plane 37. This allows the examinee 48 to take a stable image capturing posture in which the grippers 81 and 87 are gripped so that the breast insertion section 5 is placed between the arms for either of the right and left breasts 31, as in the first embodiment illustrated in FIG. 4D.

Referring next to FIGS. 10A and 10B, a ninth embodiment in which the gripper 81 includes an input device 32 for inputting an instruction from the examinee 48 will be described. FIG. 10A is an enlarged view of the gripper 81. FIG. 10B is a block diagram of the breast computed tomography system 1 including the input device 32.

As illustrated in FIG. 10A, this embodiment includes the input device 32, which is set normally off, at an end 81E of a rod-type gripper 81L attached to the side surface 4 of the gantry 2 with a pair of connecting units 82. The input device 32 is turned on when pressed by the examinee 48 to transmit an instruction on, such as an abnormal situation, to the system control unit 23.

The input device 32 is disposed to allow the examinee 48 to send his/her intention while gripping the gripper 81. The input device 32 may be disposed at any of the rod-type gripper 81L of the gripper 81, the connecting units 82, and a mount portion 33 to which the connecting units 82 are connected.

Replacing the input device 32 with a temperature sensor, a pressure sensor, a contact sensor, a photo-sensor, or any other sensor allows an instruction based on a change in gripping state to be transmitted to the system control unit 23 independent of the intention of the examinee 48. The input device 32 may include right and left cooperating input devices corresponding to the right and left grippers 81 or a combination of a plurality of cooperating sensors and switches disposed around one of the grippers 81 and may be configured to transmit cooperative instructions.

As illustrated in FIG. 109, the system control unit 23 outputs necessary instructions to the X-ray radiation unit 207, a shutter, a collimator, (not shown), and the X-ray detection unit 206 on the basis of instructions transmitted from the input device 32.

The system control unit 23 outputs an output decrease instruction or an output stop instruction to the light-emitting-unit driving unit 27 to quickly decrease or stop the output of the X-ray radiation unit 207 in accordance with the intention of the examinee 48. The system control unit 23 outputs an instruction to decrease or bring the transmittance to zero to the shutter and the collimator (not shown). This can reduce undesired exposure given to the breast 31, which is not used for image capturing. The system control unit 23 also outputs an instruction to stop the motor 71 or the X-ray detection unit 206.

The examinee 48 may have an uncomfortable feeling of the breast 31 or another region, a body motion, or the strain of muscle. This embodiment allows the examinee 48 to quickly input an instruction based on the feeling to the input device 32 close to the gripper 81L because the examinee 48 takes an image capturing posture in which the examinee 48 grips the gripper 81L.

The system control unit 23 may transmit an instruction on an abnormal situation to the display panel 29 to notify the operator of the abnormal situation. The system control unit 23 may transmit an instruction on an abnormal situation to a recording unit (not shown) or the signal processing unit 26 to associate the abnormal situation with the captured image.

At least one of the input device 32 and a sensor (not shown) may be applied to the modification of the fourth embodiment illustrated in FIG. 5E. The modification of the fourth embodiment can be further modified to a configuration (not shown) in which the posture changing unit 62 receives a slow-down instruction or a stop instruction from at least one of the input device 32 and a sensor (not shown) and slows down or stop the posture changing operation.

Since this modification allows the examinee 48 to alert the operator to problems in the examinee 48 at any time, the posture changing operation can be quickly slowed down or stopped while the image capturing posture of the examinee 48 on the examination bed is adjusted in response to the feeling of insecurity and comfortability of the examinee 48.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-249443, filed Dec. 9, 2014, which is hereby incorporated by reference herein in its entirety.

The invention claimed is:

1. A breast computed tomography system comprising:
   a light irradiation unit configured to irradiate a breast of an examinee with a light;
   a scanning unit configured to change a relative position of the light emitting unit with respect to the breast;
   a detection unit configured to detect waves extracted from a region of the breast irradiated with the light;
   a gantry accommodating the light emitting unit and the detection unit, the gantry including a front plate configured to be adjacent to the examinee;
   a breast insertion section communicating with an opening in the front plate; and
   a gripper secured to the gantry,
   wherein the gripper includes a right gripping portion and a left gripping portion.

2. The breast computed tomography system according to claim 1,
   wherein the right gripping portion and the left gripping portion are located on one side and the other side of a vertical plane, and
   wherein the vertical plane includes a central axis perpendicular to the front plate and passing through a center of the opening.

3. The breast computed tomography system according to claim 2, wherein the vertical plane is parallel to a vertical direction.

4. The breast computed tomography system according to claim 1, wherein the right gripping portion is located at a right side with respect to the opening in a direction perpendicular to a vertical plane, and the left gripping portion is located at a left side with respect to the opening in the direction perpendicular to the vertical plane.

5. The breast computed tomography system according to claim 1, further comprising:
a leg mount disposed next to the gantry and configured for the examinee to place legs,
wherein a vertical plane passes through the leg mount.

6. The breast computed tomography system according to claim 5, wherein the leg mount is disposed next to the front plate and is configured for the examinee to place at least one of thighs, lower legs, knees, and feet.

7. The breast computed tomography system according to claim 5, further comprising a posture changing unit configured to tilt the gantry and the leg mount together along the vertical plane.

8. The breast computed tomography system according to claim 7,
wherein the gantry further includes an input reception device receives an instruction based on an intention of the examinee or a sensor configured to detect a gripping state of the examinee, and
wherein an instruction to stop a posture changing operation of the posture changing unit is output in accordance with output of at least one of the input reception device and the sensor.

9. The breast computed tomography system according to claim 8, wherein at least one of the input reception device and the sensor is disposed at the gripper.

10. The breast computed tomography system according to claim 1,
wherein the gantry includes a side surface connecting to the front plate and surrounding a scanning range of the light emitting unit, and
wherein the gripper is disposed on the side surface or the front plate.

11. The breast computed tomography system according to claim 10, wherein the side surface expands in a direction away from a central axis with increasing distance from the front plate.

12. The breast computed tomography system according to claim 1, wherein the gripper is so disposed on the gantry that, for imaging a left breast, the right gripping portion is more distant from the front plate than the left gripping portion, and for imaging a right breast, the left gripping portion is more distant from the front plate than the right gripping portion.

13. The breast computed tomography system according to claim 1, further comprising a plurality of grippers secured to the gantry at different positions in a distance from the front plate along a central axis, the plurality of grippers being part of the breast computed tomography system, wherein the gripper is one of the plurality of grippers.

14. The breast computed tomography system according to claim 1, wherein the gripper extends in a direction crossing the front plate and has a certain length in the direction crossing the front plate.

15. The breast computed tomography system according to claim 14, wherein the gripper includes a proximal portion nearer to the front plate and a distal portion farther from the front plate than the proximal portion, the proximal portion being inclined at a larger angle with respect to the front plate than the distal portion.

16. The breast computed tomography system according to claim 1, wherein the gripper includes a proximal portion nearer to the front plate and a distal portion farther from the front plate than the proximal portion, the proximal portion being nearer to a central axis than the distal portion.

17. The breast computed tomography system according to claim 1, further comprising a connecting unit configured to connect, wherein the gripper is secured to the gantry via the connecting unit.

18. The breast computed tomography system according to claim 17, wherein the connecting unit includes a movable connecting portion via which the gripper is secured to the gantry at different positions varying in distance from the front plate.

19. The breast computed tomography system according to claim 18, wherein the movable connecting portion includes a guide that allows the gripper to slide along the side surface.

20. The breast computed tomography system according to claim 1, wherein the gripper extends across a vertical plane.

21. The breast computed tomography system according to claim 1, wherein the gripper includes a head side gripping portion and a leg side gripping portion which are located at a head side and at a leg side, respectively, with respect to a top-bottom segmenting plane perpendicular to a vertical plane.

22. The breast computed tomography system according to claim 1, wherein the light emitting unit includes an X-ray radiation unit configured to radiate X-rays, wherein the detection unit includes an X-ray detection unit including a plurality of X-ray detecting elements configured to output data in association with transmitted X-rays through the breast.

23. The breast computed tomography system according to claim 22, wherein the X-ray radiation unit radiates a pulsed X-ray beam.

24. The breast computed tomography system according to claim 22, further comprising a processing unit configured to perform a data processing on the data output from the X-ray detection unit so as to obtain biological information in association with an X-ray attenuation ratio transmitted through the breast.

25. The breast computed tomography system according to claim 1,
wherein the light emitting unit is an infrared irradiation unit configured to radiate infrared rays,
wherein the detection unit is an ultrasonic detection unit, and
wherein the waves are photoacoustic waves generated in the breast.

26. The breast computed tomography system according to claim 25, wherein the infrared irradiation unit performs at least one of rotational scanning, precessional scanning, spiral scanning, horizontal zigzag scanning, and raster scanning on the breast.

27. The breast computed tomography system according to claim 25, further comprising a container configured to store an acoustic impedance matching member,
wherein the detection unit detects the photoacoustic waves propagated the breast via the acoustic impedance matching member.

28. The breast computed tomography system according to claim 1, wherein the gantry includes at least one of (i) an input reception device that receives an instruction based on an intention of the examinee or (ii) a sensor configured to detect a gripping state of the examinee.

29. The breast computed tomography system according to claim 28, further comprising a system controller operably connected to at least one of the input reception device and the sensor, configured to output an instruction to decrease output of the light emitting unit in accordance with output of at least one of the input reception device and the sensor.

30. The breast computed tomography system according to claim 28, wherein at least one of the input reception device and the sensor is disposed at the gripper.

\* \* \* \* \*